United States Patent [19]

Groneberg et al.

[11] Patent Number: 5,561,143
[45] Date of Patent: Oct. 1, 1996

[54] ALIPHATIC AMINO BIS-ARYL SQUALENE SYNTHASE INHIBITORS

[75] Inventors: Robert A. Groneberg, Oaks; John R. Regan, Collegeville; Kent W. Neuenschwander, Schwenksville; Anthony C. Scotese, King of Prussia, all of Pa.

[73] Assignee: Rhone-Poulenc Rorer Pharmaceuticals Inc., Collegeville, Pa.

[21] Appl. No.: 445,631

[22] Filed: May 22, 1995

Related U.S. Application Data

[63] Continuation of Ser. No. 378,146, Jan. 25, 1995.

[51] Int. Cl.$^6$ .................. A61K 31/47; C07D 215/227; C07D 215/36; C07D 215/38
[52] U.S. Cl. .................. 514/312; 514/313; 514/314; 546/156; 546/157; 546/160; 546/161; 546/167; 546/153; 546/168; 546/173
[58] Field of Search .................. 546/156, 157, 546/160, 161, 167, 153, 168, 173; 514/312, 313, 314

[56] References Cited

U.S. PATENT DOCUMENTS

| | | | |
|---|---|---|---|
| 4,631,287 | 12/1986 | Chakraborty et al. | 514/307 |
| 4,826,838 | 5/1989 | Richardson et al. | 514/210 |
| 4,839,369 | 6/1989 | Youssefyeh et al. | 514/314 |
| 5,135,935 | 8/1992 | Alberts et al. | 514/305 |
| 5,395,846 | 3/1995 | Morris et al. | 514/375 |
| 5,455,260 | 10/1995 | Groneberg et al. | 514/375 |

FOREIGN PATENT DOCUMENTS

| | | |
|---|---|---|
| 0206751 | 12/1986 | European Pat. Off. . |
| 0219308 | 4/1987 | European Pat. Off. . |
| 9309115 | 5/1993 | WIPO . |

OTHER PUBLICATIONS

Poulter et al., J. Am. Chem. Soc., 104(25), 1982, 7376–78.
Poulter et al., J. Am. Chem. Soc., III(10), 1989, 3734–39.
Biller et al., J. Med. Chem., 31(10), 1988, 1869–71.
Sterling et al., J. Pharm. Sci., 80(8), 1991, 785–89.

*Primary Examiner*—Johann Richter
*Assistant Examiner*—Laura R. Cross
*Attorney, Agent, or Firm*—James A. Nicholson; Martin F. Savitzky; Raymond S. Parker, III

[57] ABSTRACT

This invention relates to a class of novel aliphatic amino bis-aryl compounds containing at least four carbon atoms and an amino group either substituted thereon or incorporated therein and is further linked or bridged to two mono- and/or bicyclic rings. Compounds of this invention reduce levels of serum cholesterol in the body without significantly reducing mevalonic metabolite synthesis. This invention relates also to pharmacological compositions and method of treatment for lowering serum cholesterol levels using the compounds of this invention.

8 Claims, 1 Drawing Sheet

ALIPHATIC AMINO BIS-ARYL SQUALENE SYNTHASE INHIBITORS

This is a continuation of copending application Ser. No. 08/378,146 filed on Jan. 25, 1995.

FIELD OF THE INVENTION

The present invention relates to a class of novel compounds useful in the treatment of diseases associated with undesirable cholesterol levels in the body, and particularly diseases of the cardiovascular system, such as atherosclerosis.

Only about 7% of the total body cholesterol circulates in the plasma, where it has been linked to atherosclerosis. The remaining 93% is located in cells, where it performs vital structural and metabolic functions. Excluding the diet, which accounts for approximately one-third of the total body cholesterol, the cells obtain the necessary cholesterol by endogenous biosynthesis (FIG. 1) or by removing low density lipoprotein (LDL) from the bloodstream. Approaches to the control of plasma cholesterol levels have been varied, however it has been shown that inhibiting endogenous cholesterol biosynthesis forces the cell to rely more on LDL uptake to satisfy their cholesterol requirements. Increased LDL uptake by cells, especially liver cells, has been shown to lower plasma cholesterol levels.

Squalene synthase is a microsomal enzyme that catalyzes the reductive dimerization of two molecules of farnesyl diphosphate to form squalene. While farnesyl diphosphate serves as the precursor to several other biologically important compounds, squalene is utilized only for cholesterol biosynthesis. Consequently, this is the first totally committed step in the biosynthesis of cholesterol (see FIG. 1). Inhibition at this step would stop only de novo cholesterol synthesis while allowing other essential pathways to isopentenyl tRNA, the prenylated proteins, ubiquinone, and dolichol to proceed unimpeded.

Inhibition of HMG-CoA reductase, an enzyme positioned early in the cholesterol biosynthetic pathway, results in a decrease of de novo cholesterol biosynthesis and an accompanying up-regulation of LDL receptors. However due to a large induction in the amount of the HMG-CoA reductase enzyme, the effect of this inhibition is blunted somewhat and the maximum LDL cholesterol reductions attainable are limited. Since inhibition of squalene synthase does not cause the same amount of enzyme induction (HMG-CoA reductase or squalene synthase), its inhibition results in a greater reduction of de novo cholesterol biosynthesis. This translates into more up-regulation of LDL receptors than is seen with an HMG-CoA reductase inhibitor and greater efficacy for lowering circulating LDL levels.

REPORTED DEVELOPMENTS

The literature describes the cholesterol biosynthetic pathway and possible means for the inhibition of squalene synthase. In a series of papers including *J. Am. Chem. Soc.*, 1982, 104, 7376–7378 and *J. Am. Chem. Soc.*, 1989, 111, 3734–3739, C. Dale Poulter, et al disclose that ammonium substituted cyclopropyl polyene compounds mimic the topological and electrostatic properties of the primary cation and tertiary cation of presqualene diphosphate. and in the presence of phosphate buffer, inhibit squalene synthase. Scott A. Biller et al in *J. Med. Chem.*, 1988, 31, 1869–1871 disclose that a series of stable, non-ionizable analogues of farnesyl diphosphate, comprising phosphomethylene phosphate polyene compounds, inhibit squalene synthase.

International Patent Application published under the Patent Cooperation Treaty having International Publication Number: WO 92/15579 and assigned to the same assignee as the present application, is directed to multicyclic tertiary amine polyaromatic squalene synthase inhibitors. These compounds all contain a multicyclic ring having a nitrogen atom therein.

U.S. Pat. No. 5,135,935 assigned to Merck and Co., is directed to squalene synthase inhibitors which are aryloxadiazole-quinuclidines. International Patent Applications published under the Patent Cooperation Treaty having International Publication Numbers: WO 92/12159, 92/12158, 92/12157, 92/12156 and 92/12160 and being assigned to Glaxo Group Ltd. are directed to bridged cyclic ketal derivatives for lowering the level of blood plasma cholesterol.

The present invention is directed to a class of novel alkylamino- or aminoalkyl-diaryl compounds which exhibit squalene synthase inhibition properties.

SUMMARY OF THE INVENTION

This invention comprises primary and secondary amines having attached thereto one or two aliphatic chains having a total of at least six carbon atoms and wherein each chain may further optionally contain a hetero atom selected from nitrogen, oxygen or sulfur and one chain having terminally substituted thereon a bis mono- and/or bicyclic aryl or heteroaryl ring system. The compounds of this invention possess properties which reduce levels of serum cholesterol in the body without significantly reducing mevalonic metabolite synthesis and thus provide a therapeutic agent having fewer side effects than agents which act by inhibiting the HMG-CoA recluctase enzyme. This invention relates also to pharmacological compositions and method of treatment for lowering serum cholesterol levels using the compounds of this invention.

More specifically, the compounds of this invention are described by the compounds of Formula I:

$$H-N(X)-(CR_2)_a-C(R)(Y)-(CR_2)_b-A-$$

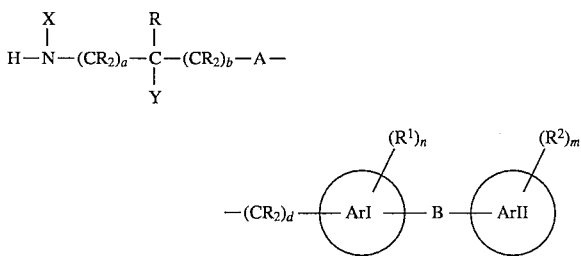

where:

X is hydrogen or —(CH$_2$)$_2$—(CR$_2$)$_f$—D—E and

Y is hydrogen or —(CR$_2$)$_h$—D—G provided one of X and Y are hydrogen;

A is O, S, NR, SO, SO$_2$, O=C, NR—C=O, O=C—NR, RC=CR, C≡C or a bond;

B is (CR$_2$)$_e$, O, S, NR, SO, SO$_2$, NR—C=O, O=C—NR, RC=CR, C≡C, O=C or a bond;

D is O, S, NR, SO, SO$_2$, O=C, CH$_2$, RC=CR or a bond;

E is —(CR$_2$)$_g$—ArIII, —CH$_2$—CH=CH—ArIII,

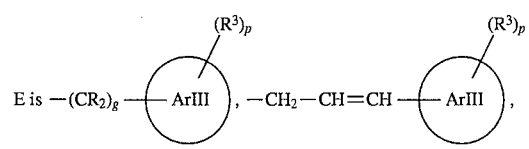

-continued

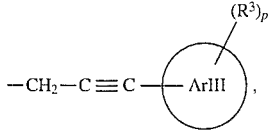

or
CH₂—CH=CR—CH₂—CH₂—CH=CR—CH₃
CH2—CR=CH—CH2—CH2—CR=CH—CH3;

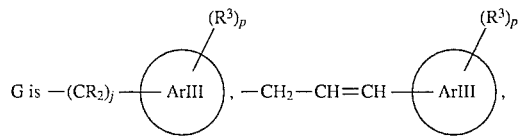

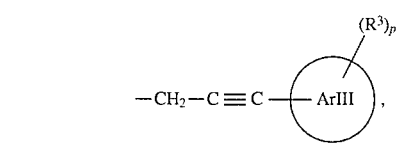

or
CH₂—CH=CR—CH₂—CH₂—CH=CR—CH₃
CH2—CR=CH—CH2—CH2—CR=CH—CH3;
CH₂—CH=CR—CH₂—CH₂—CH=CR—CH₃ or
CH₂—CR=CH—CH₂—CH₂—CR=CH—CH₃;

R is hydrogen or alkyl;
$R^1$, $R^2$ and $R^3$ are independently hydrogen, alkyl, alkoxy, hydroxy, halo, haloalkyl, nitro, amino, mono- or di-alkylamino or phenyl;
Ar I, Ar II and Ar III are aryl;
a, b and d are independently 0–3;
a+b+d is 1–3;
e is 1–3;
f and g are independently 0–4;
f+g is 3 or 4 when f and g are both present;
h and j are 0–6;
h+j is 6 or 7 when h and j are both present; and
m, n and p are 0–2; and
its stereoisomers, enantiomers, diastereoisomer and racemic mixtures; or pharmaceutically acceptable salt thereof.

DETAILED DESCRIPTION AND PREFERRED EMBODIMENTS

Figure 1:
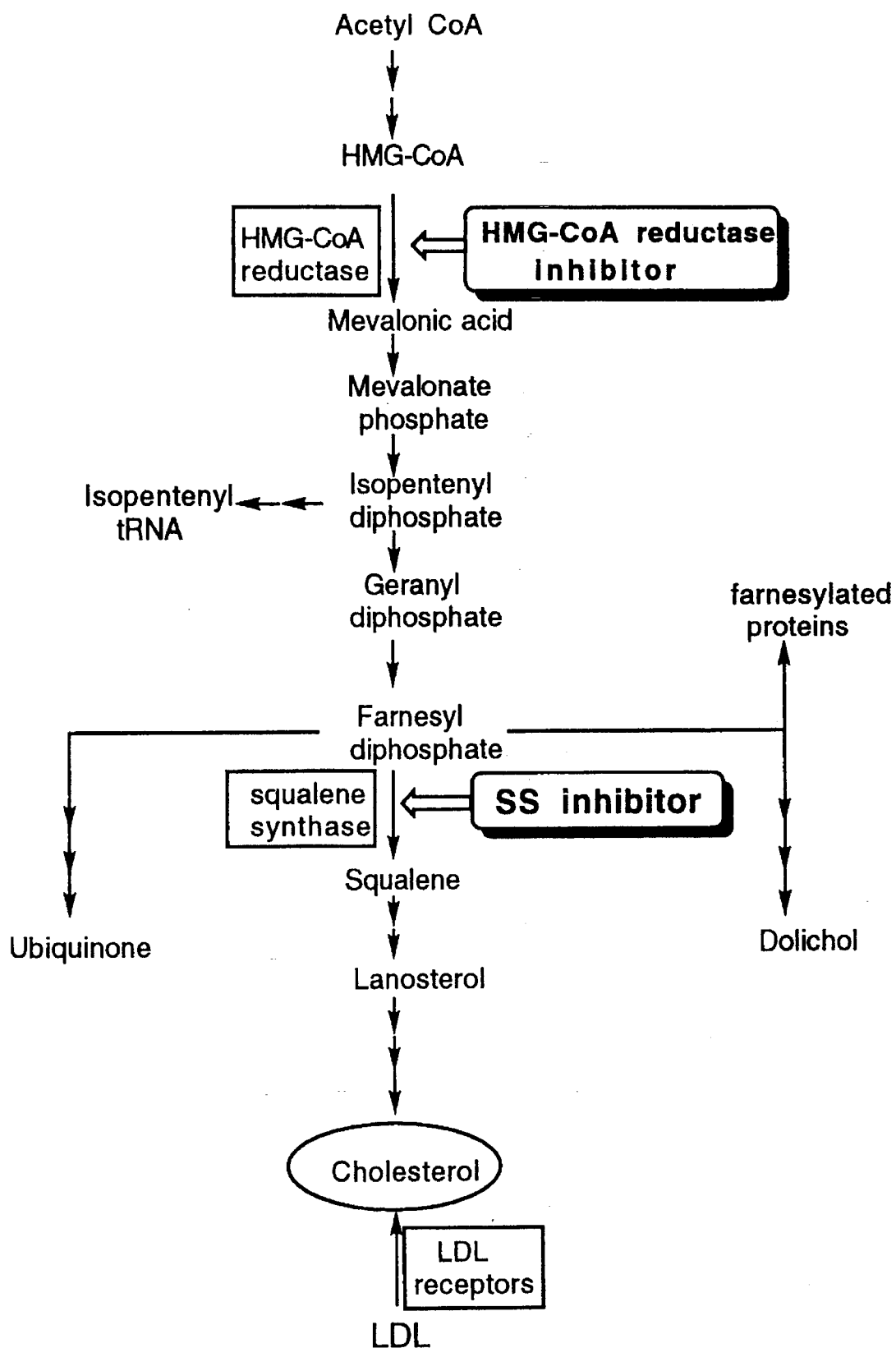
FIG. 1 is a schematic diagram of the biosynthetic pathway of cholesterol.

As employed above and throughout this disclosure, the following terms, unless otherwise indicated, shall be understood to have the following meanings:

"Aryl" means a monocylic or bicyclic carbocyclic or heterocyclic aromatic ring.

"Biological pH" refers to that pH of blood, plasma or serum in the body between about 7.2 and about 7.5 and which does not interfere with normal degradation of materials present therein. The normal pH of blood, plasma or serum values is about 7.35–7.45 and is preferably about pH 7.39–7.41.

"Monocyclic aryl" means a monocylic carbocyclic and/or heterocyclic aromatic ring. Preferred rings are substituted or unsubstituted pyrrole, thiophene, furan, imidazole, pyrazole, 1,2,4-triazole, pyridine, pyrazine, pyrimidine, pyridazine, thiazole, isothiazole, oxazole, isoxazole, s-triazine and benzene. Most preferred groups include phenyl, thienyl, pyridinyl, furyl and pyrimidinyl.

"Bicyclic aryl" means a bicyclic ring system composed of two fused carbocyclic and/or heterocyclic aromatic rings. Preferred bicyclic rings include substituted and unsubstituted indene, isoindene, benzofuran, dihydrobenzofuran, benzothiophene, indole, 1H-indazole, indoline, imidazole, azulene, tetrahydroazulene, benzofuran, benzothiaphene, benzopyrazole, benzoimadazole, benzoxazole, benzothiazole, 1,3-benzodioxole, 1,4-benzodioxan, purine, naphthalene, tetralin, coumarin, chromone, chromene, 1,2-dihydrobenzothiopyran, tetrahydrobenzothiopyran, quinoline, isoquinoline, quinazoline, pyrido[3,4-b]-pyridine, and 1,4-benzisoxazine. Most preferred groups include naphthyl, benzoxazolyl, indolyl, benzothienyl, benzofuranyl, quinolinyl and purinyl.

"Alkyl" means a saturated aliphatic hydrocarbon, either branched- or straight-chained. Preferred alkyl is "lower-alkyl" having about 1 to about 6 carbon atoms. Examples of alkyl include methyl, ethyl, n-propyl, isopropyl, butyl, sec-butyl, t-butyl, amyl and hexyl.

"Alkoxy" refers to an alkyl-O-group.

"Halo" means a halogen. Preferred halogens include chloride, bromide and fluoride. The preferred haloalkyl group is trifluoromethyl.

Preferably, Ar I and Ar II are independently a substituted or unsubstituted mono- or bicyclic aromatic ring system of about 5 to about 12 atoms. At least one ring of these systems is aromatic and the second ring of a bicyclic system may be partially or completely unsaturated carbocyclic or heterocyclic and where each ring of said system contains 0 to about 2 hetero atoms selected from N, O and S provided said hetero atoms are not vicinal oxygen and/or sulfur atoms and where the substituents may be located at any appropriate position of the ring system and are described by the R definition above.

Preferably, Ar III is phenyl or naphthyl;

The preferred compounds of this invention include those compounds of Formulae II to III:

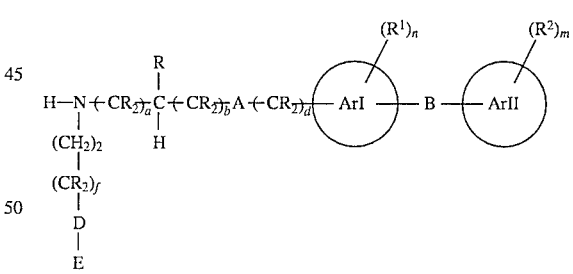

Formula II

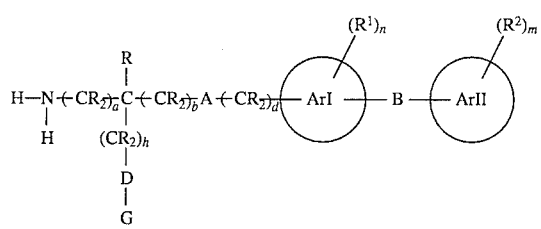

Formula III

More preferred compounds are those of Formulae II to III where:
A is O, S, NR, HC=CH or a bond;
B is $(CR_2)_e$, O, S, NR, HC=CH, O=C or a bond;

D is O, S, NR, HC=CH, CH₂C≡C or a bond;

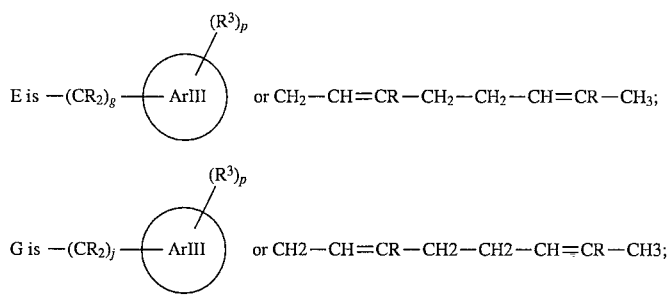

R is hydrogen or lower alkyl;
R¹, R² and R³ are independently hydrogen, alkyl, alkoxy, hydroxy, halo or haloalkyl;
a, b and d are independently 0–3;
a+b+d is 2 or 3;
e is 1–3;
f and g are independently 0–4;
f+g is 3 or 4 when f and g are both present;
h and j are independently 0–6;
h+j is 6 or 7 when h and j are both present;
m, n and p are independently 0–2;

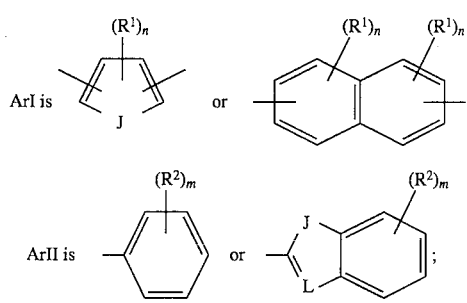

where
J is CH₂, CH=CH, O, S or N—R; and
L is CH, N or CH—O; and

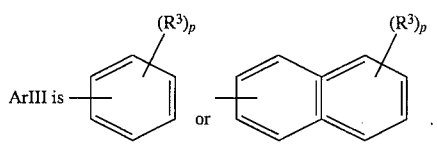

The most preferred compounds are those described by Formulae II to IV where:

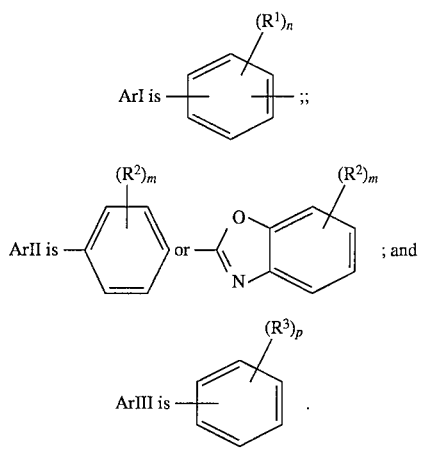

A special embodiment of this invention describes those compounds of Formulae IV to VII:

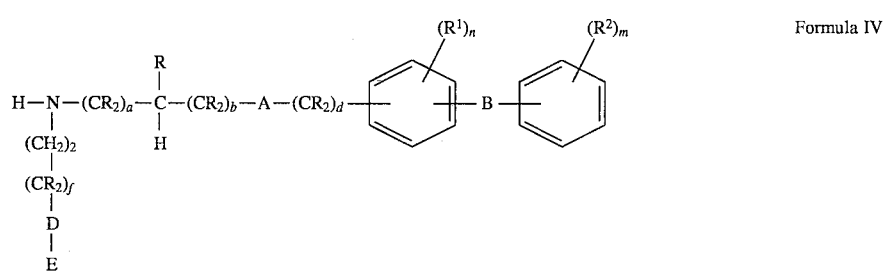

Formula IV

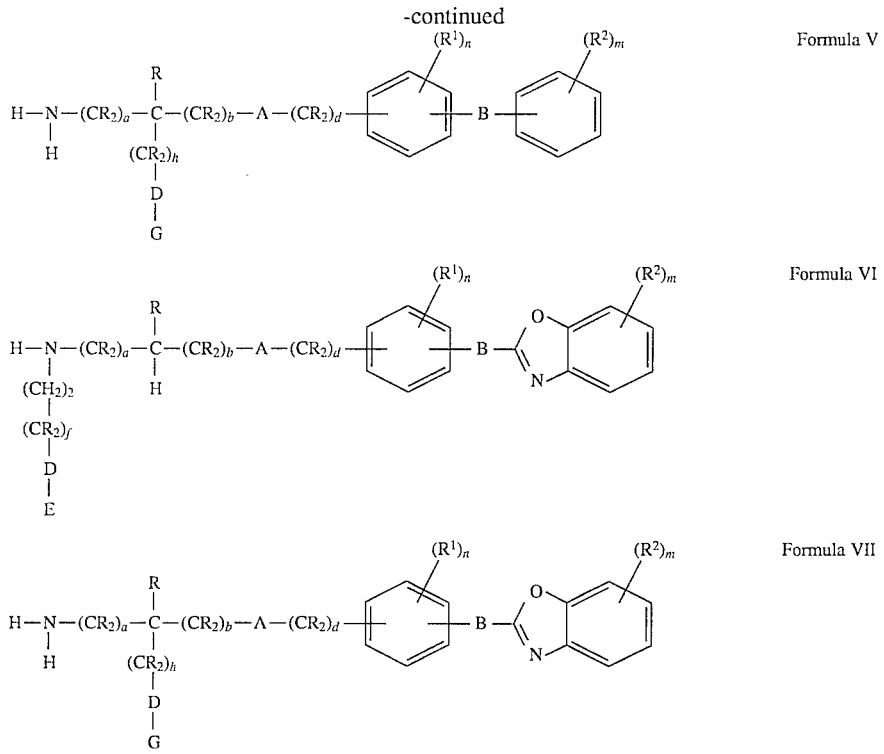

Formula V

Formula VI

Formula VII where:

A is O or a bond;
B is HC=CH, O=C or a bond;
D is O or a bond;

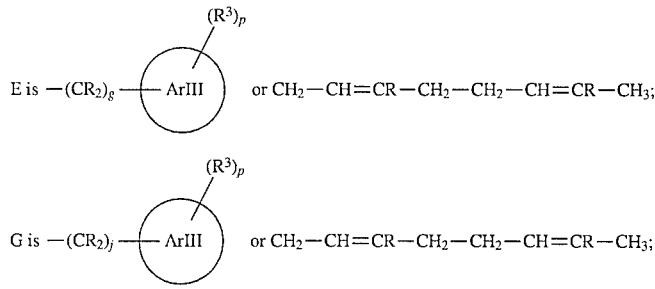

R is hydrogen or methyl;
$R^1$, $R^2$ and $R^3$ are independently hydrogen, methyl, ethyl, methoxy, ethoxy, hydroxy, chloro, bromo, fluoro or trifluoromethyl;
a, b and d are independently 0–3;
a+b+d 2 or 3;
f and g are independently 0–4; and
f+g is 3 or 4 when f and g are both present; and
h and j are independently 0–6;
h+j is 6 or 7 when h and j are both present; and
m, n and p are independently 0–2.

The compounds of this invention may be prepared by employing procedures known in the literature starting from known compounds or readily preparable intermediates Exemplary general procedures follow.

Thus, in order to prepare those compounds where A, B or D is O, S or NR the following reactions or combination of reactions are employed:

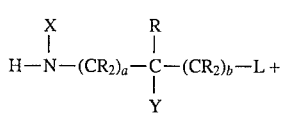

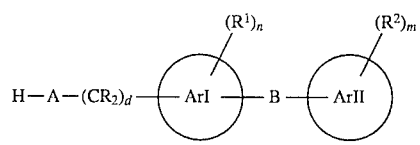

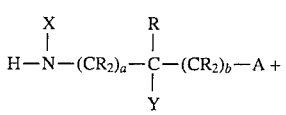

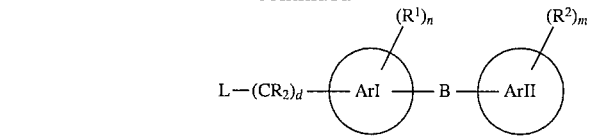
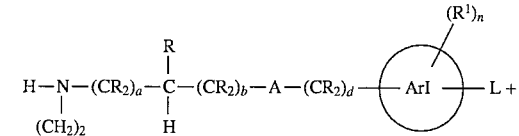
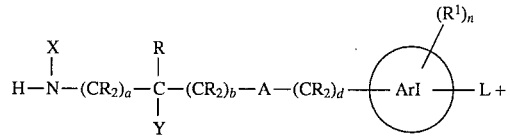
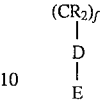
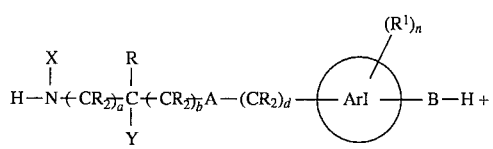
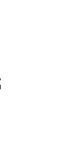
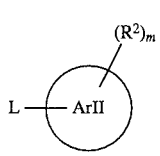
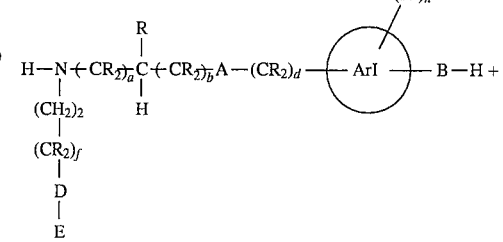
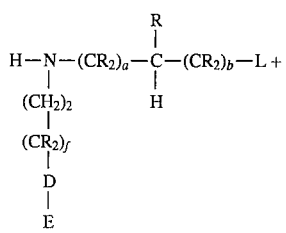
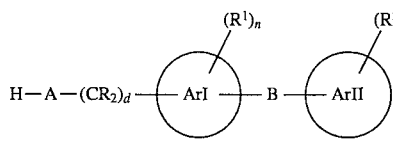
E—L+
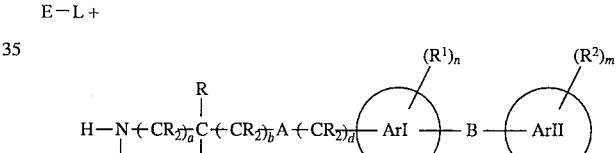
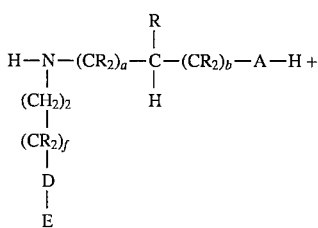
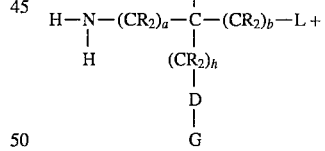
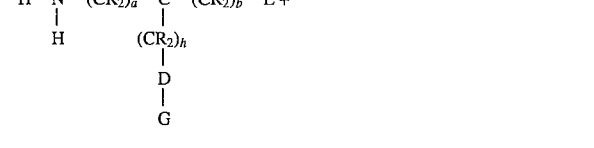
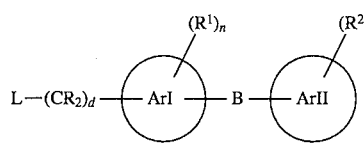
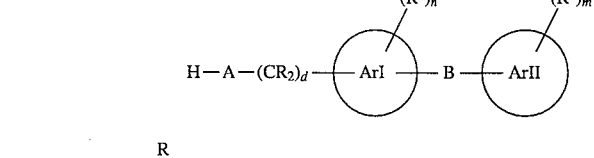
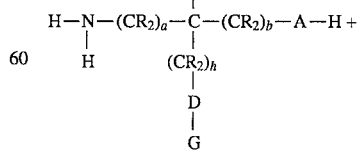
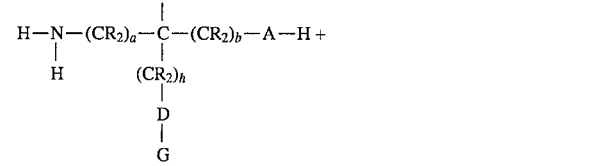

-continued

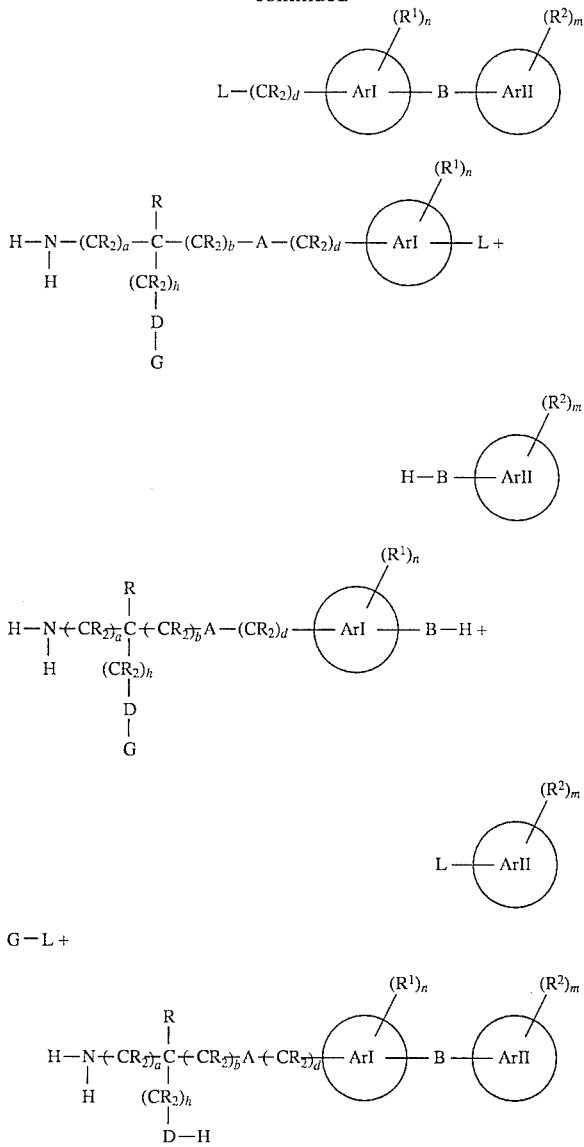

where L is a leaving group, preferably halo, tosylate or mesylate.

The amine is protected with the usual protecting groups such as trityl, t-BOC or hydroborane complex which is removed at the appropriate time with dilute acid such as HCl in the presence of a ketone, preferably acetone.

Where A, B or D are O or S, any base normally employed to deprotonate an alcohol or thiol may be used, such as sodium hydride, sodium hydroxide, triethyl amine, sodium bicarbonate or diisopropylethylamine.

Reaction temperatures are in the range of −78° C. to reflux depending on the reactants involved. (Preferably 0° C. to room temperature). Reaction times vary from about 2 to about 96 hours. The reaction is usually carried out in a solvent that will dissolve both reactants and is inert to both as well. Solvents include, but are not limited to, diethyl ether, tetrahydrofuran, N,N-dimethyl formamide, dimethyl sulfoxide, dioxane and the like.

In the case where A, B or D is SO or $SO_2$, then treatment of the thio compound with m-chlorobenzoic acid or sodium periodate results in the sulfinyl compound. Preparation of the sulfonyl compound may be accomplished by known procedures such as dissolving the sulfinyl compound in acetic acid and treating hydrogen peroxide, preferably about 30% aqueous $H_2O_2$.

In certain of the following reaction schemes a metal salt may be used. Any appropriate metal salt such as Li, K, Na, Mg, Br or the like may be used.

Those compounds where B is —C=O may be prepared by the following reaction sequence, where treatment of the substituted metal salt compound, such as the lithium, sodium potassium or Grignard compound, with an N-alkyl-N-alkoxybenzamide following the procedure of S. Nahm and S. M. Weinreb in Tet Letters, 22, 3815 (1981) results in the formation of the carbonyl chain.

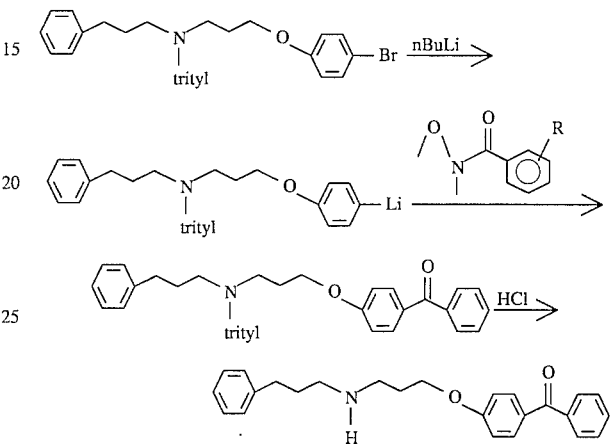

Condensation of a ketone with an appropriate hydroxylamine results in the formation of the oxime, while Wittig condensation of a ketone using $Ph_3 P=CH_2$ results in the methylene compounds; Wittig condensation also may take place at the A or D position of the molecule. This may be carried out using normal Wittig reaction conditions. When the appropriate aldehyde or ketone is reacted with a Wittig reagent then condensation results in formation of the double bond. This may then be reduced catalytically by known procedures such as Pd/C or any other suitable hydrogenating condition. The Wittig reagent is prepared by known art recognized procedures such as reaction of triphenylphosphine or diethylphosphone, with a substituted alkyl bromide followed by treatment with a strong organometallic or alkoxide base, such as n-BuLi or NaOH, results in the desired ylide. Of course this Wittig condensation may also take place when the Wittig reagent is formed on the quinuclidine position of the molecule which is then condensed with the aldehyde from the Ar III portion.

Halogenation with $Br_2$ in $CCl_4$ on the double bond followed by double dehydration with $NaNH_2$/liq $NH_3$ results in the triple bond compounds.

When A or B is —NR—CO— or —CO—NR— then condensation of an acid halide with the appropriate aniline will give the desired compound such as examples in the following schemes.

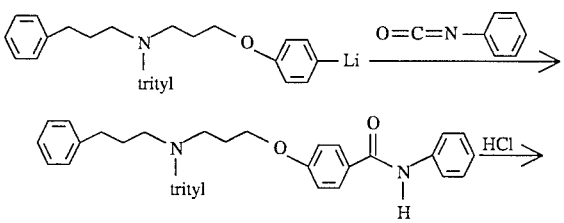

-continued

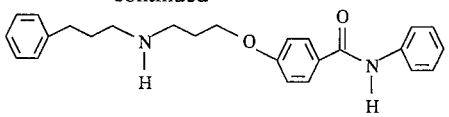

Condensation of the metal salt with a substituted phenylisocyanate results in the corresponding amide, as shown above. Reverse condensation will give the corresponding reverse amide.

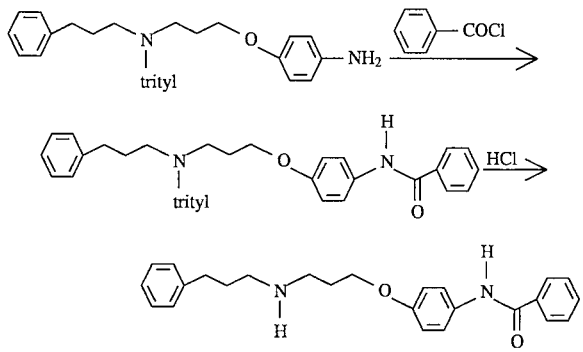

Condensation of the acid halide with the appropriate aniline will give the desired amide compound.

Condensation of the metal salt with an aldehyde or ketone followed by dehydration results in the appropriate ring addition, as shown below.

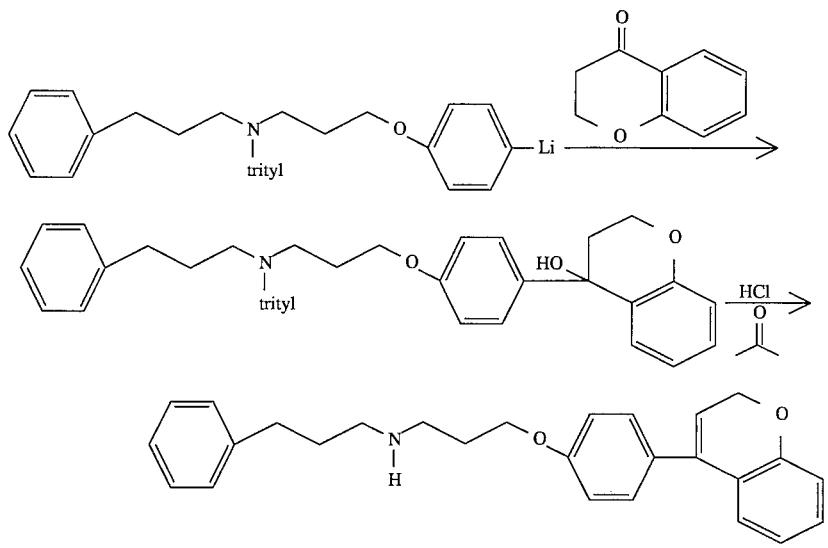

Certain compounds of this invention may have at least one asymmetric carbon atom such as those compounds having different geminal groups or those compounds which contain an asymmetric carbon atom. Further, certain compounds of this invention may exist in their cis or trans configuration such as those compounds where A, B or D is CR=CR. As a result, those compounds of this invention may be obtained either as racemic mixtures, diastereoisomeric mixtures or as individual enantiomers. When two or three asymmetric centers are present the product may exist as mixtures of two or four diastereomers. Of course it is understood that certain other compounds within the scope of this invention could have a number of stereocenters. In general, a compound with x stereocenters can have a maximum of $2^x$ stereoisomers. Therefore, a compound having three such centers gives rise to a maximum of eight stereoisomers, while one having four produces sixteen, etc. The product may be synthesized as a mixture of the isomers and then the desired isomer separated by conventional techniques such as chromatography or fractional crystallization from which each diastereomer may be resolved. On the other hand, synthesis may be carried out by known stereospecific processes using the desired form of the intermediate which would result in obtaining the desired stereospecificity.

Reference to the separation of cis and trans isomers by chromatography may be found in W. K. Chart, et al, J. Am. Chem. Soc. 96, 3642, 1974.

It is to be understood that the scope of this invention encompasses not only the various isomers which may exist but also the various mixture of isomers which may be formed.

The resolution of the compounds of this invention and their starting materials may be carried out by known procedures. Incorporation by reference is hereby made to the four volume compendium *Optical Resolution Procedures for Chemical Compounds*: Optical Resolution Information Center, Manhattan College, Riverdale, N.Y. Such procedures are useful in the practice of this invention. A further useful reference is *Enantiomers, Racemates and Resolutions*: Jean Jacques, Andre Collet and Samuel H. Wilen; John Wiley & Sons, Inc., New York, 1981. Basically, the resolution of the compounds is based on the differences in the physical properties of diastereomers. Conversion of the racemates into a mixture of diastereomers by attachment of an enantiomerically pure moiety results in forms that are separable by fractional crystallization, distillation or chromatography.

The present compounds form salts with acids when a basic amino function is present and salts with bases when an acid function, i.e., carboxyl, is present. All such salts are useful in the isolation and/or purification of the new products. Of particular value are the pharmaceutically acceptable salts with both acids and bases. Suitable acids include, for example, hydrochloric, sulfuric, nitric, benzenesulfonic, toluenesulfonic, acetic, maleic, tartaric and the like which are pharmaceutically acceptable. Basic salts for pharmaceutical use are the Na, K, Ca and Mg salts.

Various substituents on the present new compounds can be present in the starting compounds, added to any one of the intermediates or added after formation of the final products by known methods of substitution or conversion reactions. If the substituents themselves are reactive, then the substituents can themselves be protected according to the techniques known in the art. A variety of protecting groups known in the art, may be employed. Examples of many of these possible groups may be found in "Protective Groups in Organic Synthesis" by T. W. Green, John Wiley and Sons, 1981. For example, nitro groups can be added by nitration and the nitro group converted to other groups, such as amino by reduction, and halo by diazotization of the amino group and replacement of the diazo group. Acyl groups can be added by Friedel-Crafts acylation. The acyl groups can then be transformed to the corresponding alkyl groups by various methods, including the Wolff-Kishner reduction and Clemmenson reduction. Amino groups can be alkylated to form mono- and di-alkylamino groups; and mercapto and hydroxy groups can be alkylated to form corresponding ethers. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

Since the compounds of this invention have certain substituents which are necessarily present, the introduction of each substituent is, of course, dependent on the specific substituents involved and the chemistry necessary for their formation. Thus, consideration of how one substituent would be affected by a chemical reaction when forming a second substituent would involve techniques familiar to the skilled artisan. This would further be dependent on the ring involved.

The compounds of the present invention may be prepared by the following representative examples.

EXAMPLE 1

N-[2-(4-(benzoxazol-2-yl)benzyloxy)ethyl]-
2-[3-(4-methylphenyl)prop- 2-ynyloxy]ethanamine
hydrochloride Step A 4-(benzoxazol-2-yl)benzyl alcohol To 500 ml THF cooled to −78° C. is added butyl lithium (2 eq.) followed by 4-bromobenzyl alcohol (27.2 g; 145 mmol) slowly over 45 minutes in a solution of THF (100 ml) keeping the temperature below −72° C. After 10 minutes following the final addition of the alcohol is added 2-chlorobenzoxazole (23.3 g; 145 mmol) in 25 ml THF slowly over 45 minutes. The temperature is maintained at −78° C. for 1 hour and then warmed to −40° C. for 15 minutes. The reaction is then quenched with 15 ml of acetic acid and allowed to warm to room temperature, diluted with 800 ml ether, washed 3× with $H_2O$ and brine, dried ($MgSO_4$) and concentrated in vacuo to obtain a brown oily solid which is washed with 400 ml petroleum ether and filtered to obtain 4-(benzoxazol-2-yl)benzyl alcohol as a tan solid which is used directly in Step B.

Step B 4-(benzoxazol-2-yl)benzyl bromide

To 4-(benzoxazol-2-yl)benzyl alcohol (20.9 g; 100 mmol) dissolved in $CH_2Cl_2$ (330 ml) and cooled to 0°–5° C. is added thionyl bromide (9.2 ml; 120 mmol) and allowed to warm to room temperature after removing the bath. After 1½ hours, 2,6-lutidine (11.6 ml; 100 mmol) is added to the mixture and warmed to 30° C. The reaction mixture is then diluted with $CH_2Cl_2$, washed with $H_2O$ 1×, 0.2M HCl 1×, $NaHCO_3$ 2×, brine, dried ($MgSO_4$) and concentrated to dryness. The residue is recrystallized from EtOAc to obtain 4-(benzoxazol-2-yl)benzyl bromide as white-orange needles which is used directly in Step C.

Step C N-trityl-N,N-diethanolamine

Diethanolamine (22.2 g; 211 mmol) and triethylamine (39.3 g; 141 mmol) are dissolved in a solution of $CH_2Cl_2$ (150 ml) and cooled to 0° C. Tritylchloride is then added portionwise over 5 minutes and the reaction mixture is stirred for 4 hours, diluted with 100 ml $CH_2Cl_2$ and washed with water 3×, dried ($Na_2SO_4$), triturated with ether, concentrated to dryness and recrystallized from EtOAc to obtain N-trityl-N,N-diethanolamine which is used directly in Step D.

Step D N-trityl-N-[2-(4-(benzoxazol-2-yl)benzyloxy)ethyl]-2-hydroxyethanamine

N-trityl-N,N-diethanolamine (9 g; 25.9 mmol) is dissolved in THF (50 ml) and is cooled to 0° C. NaH (1 g; 26 mmol) is then added and stirred at room temperature for 1 hour. 4-(Benzoxazol-2-yl)benzyl bromide is added and stirred overnight. The reaction mixture is concentrated, diluted with $CH_2Cl_2$, washed with $H_2O$ 2×, brine, dried ($Na_2SO_4$) and concentrated to dryness. The resultant residue is purified by column chromatography using 10 $Et_3N$/10 $CH_2Cl_2$/80 PE to obtain N-trityl-N-[2-(4-(benzoxazol-2-yl)benzyloxy)ethyl]-2-hydroxyethanamine which is used directly in Step E.

Step E N-trityl-N-[2-(4-(benzoxazol-2-yl)benzyloxy)ethyl]-2-(prop-2-ynyloxy)ethanamine Dry N-trityl-N-[2-(4-(benzoxazol-2-yl)benzyloxy)ethyl]-2-hydroxyethanamine (8.7 g; 15.7 mmol) is dissolved in THF (50 ml). NaH (1 g; 25 mmol) is added and stirred vigorously at 0° C. for 1 minute then brought to room temperature for 45 minutes. DMPU [1,3-dimethyl-3,4,5,6-tetrahydro-2(1H)pyrimidinone] (5 ml) is added followed by propargyl bromide (80 wt %/toluene; 2.1 ml) and stirred for 48 hours. To this is added 0.6 g NaH and 1.5 ml propargyl bromide. After stirring vigorously, an additional 48 hours the reaction mixture is quenched with MeOH, concentrated and purified by column chromatography using 10 $Et_3N$/10 $CH_2Cl_2$/80 petroleum ether. The product is triturated with ether to give solid N-trityl-N-[2-(4-(benzoxazol-2-yl)benzyloxy)ethyl]-2-(prop-2-ynyloxy)ethanamine which is used directly in Step F.

Step F N-trityl-N-[2-(4-(benzoxazol-2-yl)benzyloxy)ethyl]-2-[3-(4-methylphenyl)prop- 2-ynyloxy]ethanamine N-trityl-N-[2-(4-(benzoxazol-2-yl)benzyloxy)ethyl]-2-(prop-2-ynyloxy)ethanamine (0.517 g; 0.87 mmol), 4-iodotoluene (0.262 g; 1.2 mmol) and copper (I) iodide (3.5 mg; 2%/wt) are dissolved in $BuNH_2$ (4 ml) in an inert atmosphere (argon). To this is added $(PPh_3)_2PdCl_2$, [bis(triphenylphosphine)palladium chloride], (6 mg; 1%/wt) and the reaction is heated at 75° C. for 1 hour. The mixture is then concentrated in vacuo and purified by column chromatography using 10 $Et_3N$/10 $CH_2Cl_2$/PE to obtain N-trityl-N-[2-(4-(benzoxazol-2-yl)benzyloxy)ethyl]-2-[3-(4-methylphenyl)prop-2-ynyloxy]ethanamine which is used directly in Step G.

Step G N-[2-(4-(benzoxazol-2-yl)benzyloxy)ethyl]-2-[3-(4-methylphenyl)prop- 2-ynyloxy]ethanamine hydrochloride N-trityl-N-[2-(4-(benzoxazol-2-yl)benzyloxy)ethyl]-2-[3-(4-methylphenyl)-2-propynyloxy]ethanamine (600 mg) is dissolved in a solution of $CH_2Cl_2$ (10 ml) and EtOH (10 ml) and is treated with a solution of EtOH/HCl until acidic by pH paper. The solution is concentrated in vacuo, then purified by column chromatography using 5% MeOH/

CH$_2$Cl$_2$. The residue is isolated, dissolved in methanol and acidified with acidic methanol. The solution is concentrated to obtain N-[2-(4-(benzoxazol-2-yl)benzyloxy)ethyl]-2-[3-(4-methylphenyl)prop-2-ynyloxy]ethanamine hydrochloride (m.p. 161°–162° C.).

EXAMPLE 2

When 4-(benzoxazol-2-yl)benzyl bromide in Example 1, Step D is replaced by the following compounds:
4-biphenylmethyl bromide
3-biphenylmethyl bromide
2-biphenylmethyl bromide
4-styrylbenzyl bromide
4-(cyclohexen-1-yl)benzyl bromide
4-phenylmethoxybenzyl bromide
3-phenoxybenzyl bromide
3,4-dichlorophenoxybenzyl bromide
3-(4-t-butylphenoxy)benzyl bromide
4-(3,3,5,5-tetramethylcyclohexen-1-yl)benzyl bromide
4-(4,4,6,6-tetramethylcyclohexen-1-yl)benzyl bromide
4-(4,4-dimethylcyclohexyl-1-yl)benzyl bromide
4-chlorobenzoylbenzyl bromide
4-(1-phenethenyl)benzyl bromide
4-(2-phenylethyl)benzyl bromide
2-benzoylbenzyl bromide
3-benzyloxybenzyl bromide
2-phenethylbenzyl bromide
4-(2,5-dimethylstyryl)benzyl bromide
4-(3,4-dichlorostyryl)benzyl bromide
4-(4-fluorostyryl)benzyl bromide
4-phenoxybenzyl bromide
4-((1-benzoyl-1-methyl)ethyl)benzyl bromide
4-benzoylbenzyl bromide
N-methylbenzamidobenzyl bromide
4-phenylethynylbenzyl bromide
4-(1-(4-chlorophenyl)ethenyl)benzyl bromide
4-(1-(2-chlorophenyl)ethenyl)benzyl bromide
4-(4-methylphenylsulfonyl)benzyl bromide
3-benzoylbenzyl bromide
4-(benzoxazol-2-yl)benzyl bromide
then their corresponding products are prepared.

EXAMPLE 3

When iodotoluene in Example 1, Step F is replaced with the following compounds:

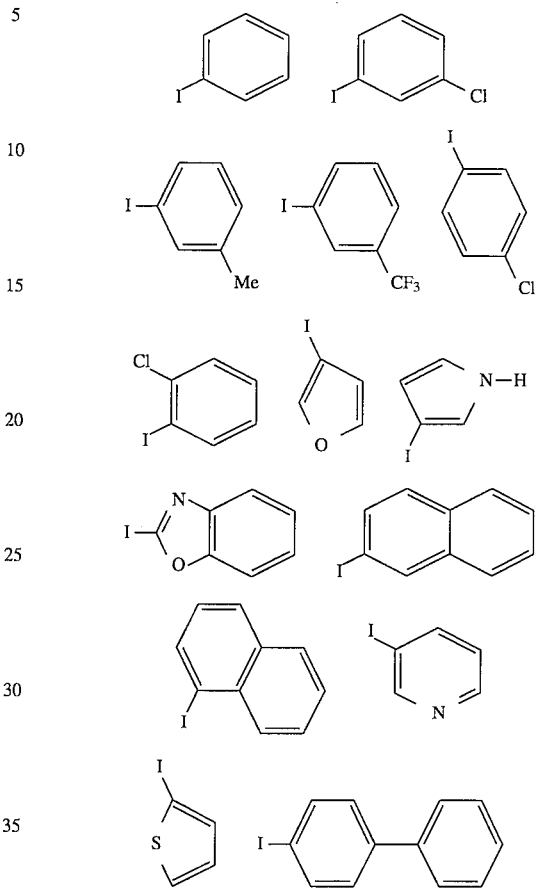

then their corresponding products are prepared.

EXAMPLES 4–12

When the products prepared in example 3 are used in example 1, Step G, then the corresponding products are prepared.

| Example | | m.p. |
|---|---|---|
| 4 | 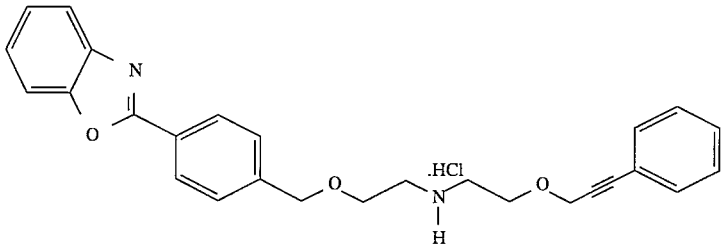 | 127–130° C. |

-continued
| Example | | m.p. |
|---|---|---|
| 5 | 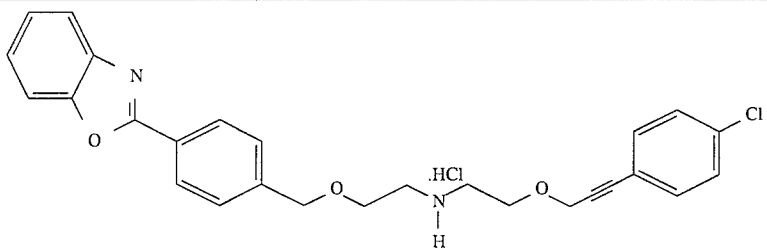 | 170–171° C. |
| 6 | 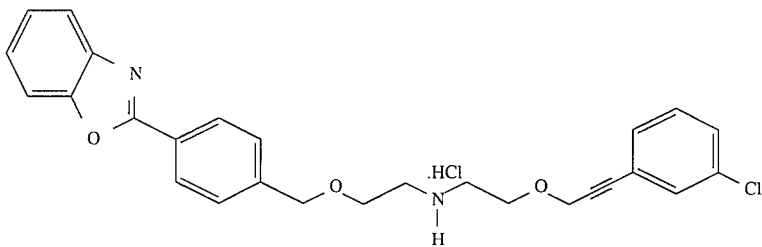 | 140–142° C. |
| 7 | 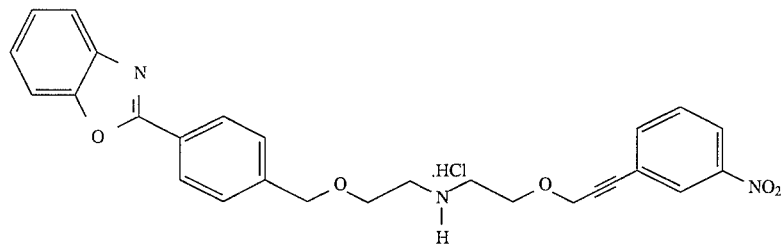 | 136–138° C. |
| 8 | 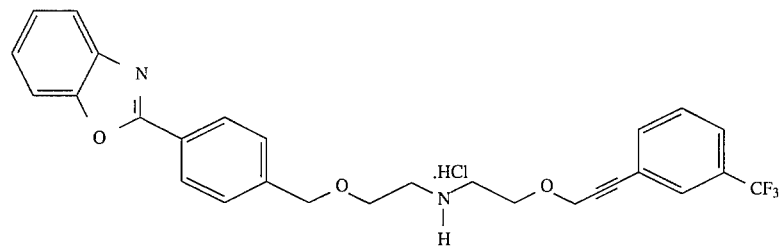 | 145–148° C. |
| 9 | 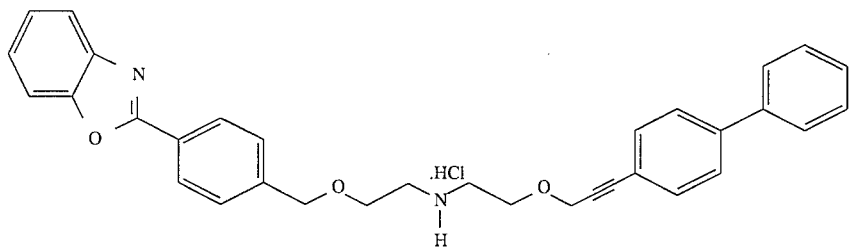 | 195–197° C. |
| 10 | 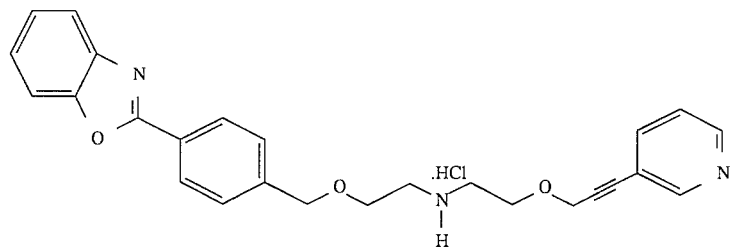 | 126–128° C. |

-continued

| Example | Structure | m.p. |
|---|---|---|
| 11 | benzoxazole-C6H4-CH2-O-CH2CH2-NH·HCl-CH2CH2-O-C≡C-(2-naphthyl) | 154–155° C. |
| 12 | benzoxazole-C6H4-CH2-O-CH2CH2-NH·HCl-CH2CH2-O-C≡C-(2-thienyl) | 126–130° C. |

EXAMPLE 13

N-[2-(4-(benzoxazol-2-yl)benzyloxy)ethyl]-2-[3-(4-methylphenyl)propoxy]ethanamine hydrochloride N-[2-(4-(benzoxazol-2-yl)benzyloxy)ethyl]-2-[3-(4-methylphenyl)prop-2-ynyloxy]ethanamine hydrochloride (125 mg) is dissolved in MeOH (12 ml) in an argon atmosphere and then 27 mg Pd/C catalyst is added. H$_2$ is bubbled into the reaction mixture for 1 minute and stirred under H$_2$ for 20 minutes. The mixture is purged with argon and filtered through celite and washed with MeOH and THF. Several drops of HCl/EtOH are added until acidic and the mixture concentrated to dryness to obtain N-[2-(4-(benzoxazol-2-yl)benzyloxy)ethyl]-2-[3-(4-methyl-phenyl)propoxy]ethanamine hydrochloride as a white solid. (m.p. 138°–139° C.).

EXAMPLES 14–31

Following the procedure of Example 13 the following compounds are prepared.

| Example | Structure | m.p. |
|---|---|---|
| 14 | benzoxazole-C6H4-CH2-O-CH2CH2-NH·HCl-CH2CH2-O-CH2CH2CH2-(3-chlorophenyl) | 105–109° C. |
| 15 | benzoxazole-C6H4-CH2-O-CH2CH2-NH·HCl-CH2CH2-O-CH2CH2CH2-(3-methylphenyl) | 122–125° C. |

| Example | | m.p. |
|---|---|---|
| 16 | benzoxazole-C6H4-CH2-O-CH2CH2-NH·HCl-CH2CH2-O-CH2CH2CH2-C6H4-3-CF3 | 108–109° C. |
| 17 | benzoxazole-C6H4-CH2-O-CH2CH2-NH·HCl-CH2CH2-O-CH2CH2CH2-C6H4-4-Cl | 129–130° C. |
| 18 | benzoxazole-C6H4-CH2-O-CH2CH2-NH·HCl-CH2CH2-O-CH2CH2CH2-C6H4-2-Cl | 108–111° C. |
| 19 | benzoxazole-C6H4-CH2-O-CH2CH2-NH·HCl-CH2CH2-O-CH2CH2CH2-C6H5 | 130–132° C. |
| 20 | benzoxazole-C6H4-CH2-O-CH2CH2-NH·HCl-CH2CH2-O-CH2CH2CH2-(3-biphenyl) | 117–118° C. |
| 21 | benzoxazole-C6H4-CH2-O-CH2CH2-NH·HCl-CH2CH2-O-CH2CH2CH2CH2-C6H5 | 130–131° C. |

-continued
| Example | | m.p. |
|---|---|---|
| 22 | 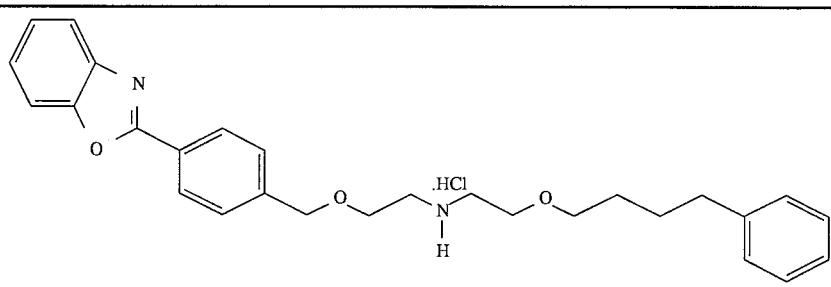 | 121–125° C. |
| 23 | 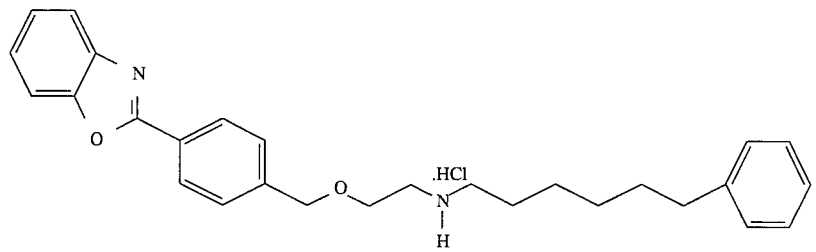 | 163–165° C. |
| 24 | 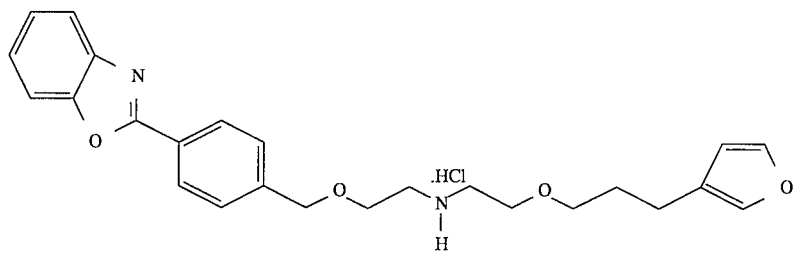 | |
| 25 | 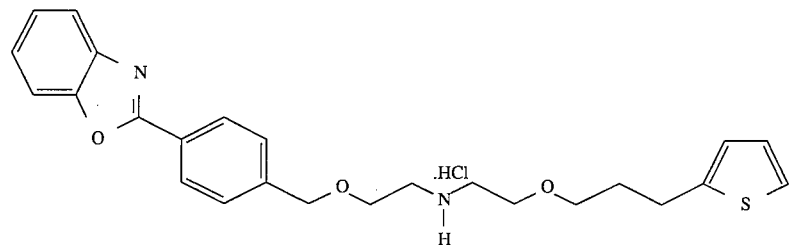 | 122–125° C. |
| 26 | 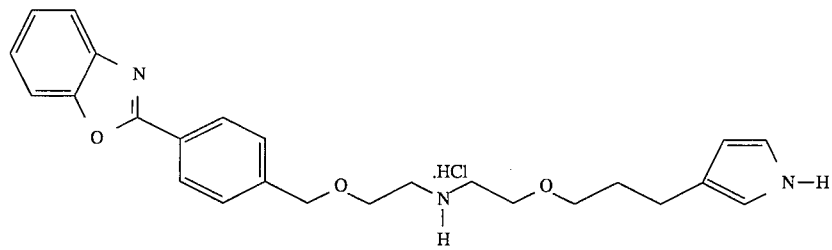 | |
| 27 | 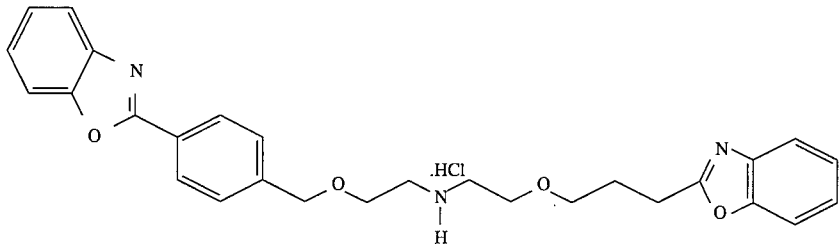 | |

-continued

| Example | | m.p. |
|---|---|---|
| 28 | [structure: benzoxazole-phenyl-CH2-O-CH2CH2-NH·HCl-CH2CH2-O-CH2CH2CH2-(2-naphthyl)] | 146–150° C. |
| 29 | [structure: benzoxazole-phenyl-CH2-O-CH2CH2-NH·HCl-CH2CH2-O-CH2CH2CH2-(1-naphthyl)] | 113–115° C. |
| 30 | [structure: benzoxazole-phenyl-CH2-O-CH2CH2-NH·HCl-CH2CH2-O-CH2CH2CH2-(3-pyridyl)] | |
| 31 | [structure: benzoxazole-phenyl-CH2-O-CH2CH2-NH·HCl-CH2CH2-O-CH2CH2CH2-(4-methylphenyl)] | 138–139° C. |

EXAMPLE 32

N-[2-(4-(benzoxazol-2-yl)benzyloxy)ethyl]-2-(4-phenylbutoxy)ethanamine hydrochloride Step A N-trityl-N-[2-(4-(benzoxazol-2-yl)benzyloxy)ethyl]-2-(4-phenylbutoxy)ethanamine To N-trityl-N-[2-(4-(benzoxazol-2-yl)benzyloxy)ethyl]-2-hydroxyethanamine (0.205 g; 0.37 mmol) dissolved in dry THF (2 ml) is added NaH (60% in oil; 38 mg; 0.95 mmol) at room temperature. After 1 hour, DMPU, [1,3-dimethyl-3,4,5,6-tetrahydro-2(1H)-pyrimidinone] (0.5 ml) and 4-phenyl-1-butyl iodide (0.19 g; 0.74 mmol) are added. After 15 minutes, the reaction mixture is heated at 60° C. for 2 hours. The mixture is then cooled, quenched with MeOH, diluted with $CH_2Cl_2$ washed $H_2O$ 2x, brine 1x, dried ($Na_2SO_4$), concentrated to dryness and purified by column chromatography with 5% $Et_3N$/5% $CH_2Cl_2$/90% petroleum ether to obtain N-trityl-N-[2-(4-(benzoxazol-2-yl)benzyloxy)ethyl]-2-(4-phenylbutoxy)]-ethanamine as an oil which is used directly in Step B.

Step B N-[2-(4-(benzoxazol-2-yl)benzyloxy)ethyl]-2-(4-phenylbutoxy)ethanamine hydrochloride N-trityl-N-[2-(4-(benzoxazol-2-yl)benzyloxy)ethyl]-2-(4-phenylbutoxy)ethanamine (600 mg) is dissolved in a solution of $CH_2Cl_2$ (10 ml) and EtOH (10 ml) and treated with a solution of EtOH/HCl until acidic by pH paper. The solution is concentrated in vacuo, then purified by column chromatography using 5% MeOH/$CH_2Cl_2$. The residue is isolated, dissolved in methanol and acidified with acidic methanol. The solution is concentrated to obtain N-[2-(4-(benzoxazol-2-yl)benzyloxy)ethyl]-2-(4-phenylbutoxy)ethanamine hydrochloride (m.p. 121°–125° C.).

EXAMPLE 33

N-[2-(4-(benzoxazol-2-yl)benzyloxy)ethyl]-2-(3-phenylprop- 2-enyloxy)ethanamine hydrochloride When the procedures of example 32 is followed and 4-phenyl-1-butyl iodide of Step A is replaced with 3-bromo-1-phenylpropene then the product prepared is N-[2-(4-(benzoxazol-2-yl)benzyloxy)ethyl]-2-(3-phenylprop-2-enyloxy)ethanamine hydrochloride (m.p. 145°–147° C.).

EXAMPLE 34

N-[2-(4-(benzoxazol-2-yl)benzyloxy)ethyl]-6-phenylhexanamine hydrochloride

Step A N-tritylethanolamine

Ethanolamine hydrochloride (9.9 g; 100 mmol) is partially dissolved in $CH_2Cl_2/CH_3CN$ (200 ml/100 ml) and $Et_3N$ (23 ml; 170 mmol) is then added. Tritylchloride (18.9 g; 67.6 mmol) is added portionwise over 30 minutes. After the addition is complete the reaction mixture is allowed to stir an additional 30 minutes, diluted with $CH_2Cl_2$, washed With $H_2O$ 2× and brine, dried ($MgSO_4$), concentrated in vacuo and purified by column chromatography with silica/$CH_2Cl_2$ to give N-tritylethanolamine as an oil which is used directly in Step B.

Step B N-trityl-2-[(4-(benzoxazol-2-yl)benzyloxy)ethylamine

N-tritylethanolamine (7.1 g; 23.4 mmol) is dissolved in THF (80 ml) and cooled to 0° C. NaH (60%/wt.; 1.4 g; 35 mmol) is then added and the reaction mixture is warmed at 45° C. for 1 hour, and then cooled to room temperature and stirred for 1 hour. To this is added 4-(benzoxazol-2-yl)benzyl bromide (6.05 g; 21 mmol) and allowed to stir overnight. MeOH is added to quench any excess NaH. The reaction mixture is concentrated in vacuo, dissolved in 500 ml $CH_2Cl_2$, washed with $H_2O$ and brine, dried ($MgSO_4$) and concentrated to dryness. The residue is washed with EtOH and filtered to obtain N-trityl-2-(4-[(benz-oxazol-2-yl)benzyloxy)]ethylamine as a white solid which is used directly in Step C.

Step C 2-[4-(benzoxazol-2-yl)benzyloxy]ethylamine hydrochloride

N-trityl-2-[4-(benzoxazol-2-yl)benzyloxy]ethylamine (9.1 g; 17.8 mmol) is suspended in EtOH and treated with HCl/EtOH until acidic by pH paper. The reaction mixture is heated at 80° C. for 3 hours keeping the reaction acidic. The reaction mixture is then cooled and the solid is filtered and washed with EtOH to give 2-[4-(benzoxazol-2-yl)benzyloxy]ethylamine hydrochloride (m.p. 232°–233° C.) as a white solid which is used directly in Step F.

Step D 6-phenylhex-1-yl methylsulfonate

To 6-phenyl-1-hexanol (3.2 g; 18 mmol) dissolved in $CH_2Cl_2$ (60 ml) is added $Et_3N$ (3.7 ml) and the solution is cooled to 0° C. Methanesulfonyl chloride (1.5 ml; 20 mmol) is added dropwise and then the reaction mixture is allowed to stir for 30 minutes at 0° C. This is then diluted with $Et_2O$ and washed with 2N HCl, $NaHCO_3$ solution 2× and brine, dried ($MgSO_4$) and concentrated to dryness to obtain 6-phenylhex-1-yl methylsulfonate as an oil which is used directly in Step E Step E 6-phenyl-1-hexyl iodide To 6-phenylhex-1-yl methylsulfonate (4.55 g; 17.3 mmol) dissolved in acetone (100 ml) is added sodium iodide (2.5 g; 173 mmol) and the reaction mixture is heated 2 hours at reflux. The reaction mixture is then concentrated to dryness and partitioned between ether and water. The organic phase is separated, dried, concentrated to dryness and purified with silica chromatography using 10 EtOAc/90 petroleum ether to give 6-phenyl-1-hexyl iodide as a colorless oil which is used directly in Step F.

Step F N-[2-(4-(benzoxazol-2-yl)benzyloxy)ethyl]-6-phenylhexanamine hydrochloride To a solution of 6-phenyl-1-hexyl iodide (0.63 g; 2.2 mmol) in THF (12 ml) is added 2-[4-(benzoxazol-2-yl)benzyloxy]ethylamine hydrochloride (0.6 g ; 2 mmol) followed by NaH (60% suspension; 0.11 g). The reaction mixture is stirred for 1 hour at room temperature and then heated for 1½ hours at reflux. The mixture is next cooled, acidified with HCl/EtOH, concentrated and purified by column chromatography using 10% $MeOH/CH_2Cl_2$ as eluant. The resultant product is treated with HCl/EtOH and recrystallized from EtOH to give pure N-[2 -(4-(benzoxazol-2-yl)benzyloxy)ethyl]-6-phenyl-1-hexanamine hydrochloride. (m.p. 163°–165° C.).

EXAMPLE 35

When 6-phenyl-1-hexanol in the Example 34, Step D is replaced by the following compounds:

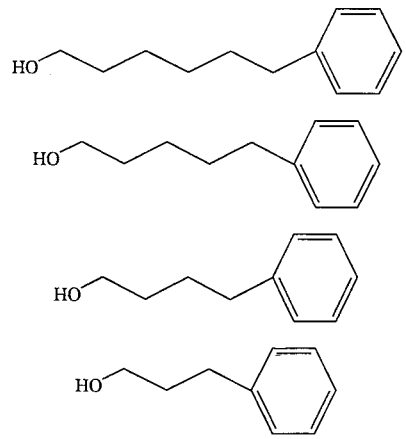

then their corresponding product is prepared.

EXAMPLE 36

N-[2-(4-(benzoxazol-2-yl)benzyloxy)ethyl]-3-(2-phenylethoxy)propanamine hydrochloride Step A 2-allyloxyethylbenzene To a solution of 2-phenylethanol (9.09 g; 72.9 mmol) dissolved in THF (75 ml) and cooled to 0° C. is added NaH (60%; 3.5 g; 87 mmol) in portions over 10 minutes. The mixture is allowed to warm to room temperature, stirred for 45 minutes and cooled. Allyl bromide (6.3 ml; 73 mmol) is added and the mixture is brought to room temperature and stirred vigorously. The reaction mixture is heated at 45° C. for 3 hours, quenched with MeOH, diluted with $Et_2O$, washed with $H_2O$ 3× and brine, dried ($MgSO_4$) and concentrated to dryness. The resultant yellow oil is purified by column chromatography using 10% ether/petroleum ether to give 2-allyloxyethylbenzene as a clear oil which is used directly in Step B.

Step B 3-(2-phenylethoxy)-1-propanol

To a cooled (0° C.) solution of 2-allyloxyethylbenzene (5. g; 30.8 mmol) dissolved in THF (75 ml) is slowly added a 0.5M THF solution of 9-BBN [9-borabicyclo[3.3.1]nonane] (68 ml; 34 mmol) and the reaction mixture warmed to room temperature and stirred for 4 hours. The reaction mixture is then cooled to 0° C. and 5 ml $H_2O$ is added followed by slow addition of 6N NaOH (30 ml; 7.2 g/30 ml). After stirring for 5 minutes, 30% $H_2O_2$ (20 ml)is added over 15 min. The reaction mixture warms significantly but is kept from refluxing. After addition is complete, it is stirred for 15 minutes allowing the mixture to come to room temperature. It is then diluted with $Et_2O$, washed with $H_2O$ 2×, $Na_2S_2O_3$ 2×, $NaHCO_3$ and brine, dried ($MgSO_4$) and concentrated to dryness. The residue is purified by column chromatography using Et$_2$O to obtain 3-(2-phenylethoxy)-1-propanol which is used directly in Step C.

Step C 1-iodo-3-(2-phenylethoxy)propane

To 3-(2-phenylethoxy)-1-propanol (2 g; 11 mmol) dissolved in toluene (50 ml), acetonitrile (50 ml), imidazole (2.2 g; 33 mmol) and triphenylphosphine (2.8 g; 11 mmol) is added iodine (2.8 g; 11 mmol). The reaction mixture is heated for 1 hour at 50° C., then it is cooled, diluted with Et$_2$O, washed with 1N HCl, NaS$_2$O$_3$ solution, NaHCO$_3$ and brine, dried (MgSO$_4$) and concentrated in vacuo to dryness. The residue is purified by column chromatography using 10% ether/90% petroleum ether to obtain 1-iodo-3-(2-phenylethoxy)propane which is used directly in Step D.

Step D N-[2-(4-(benzoxazol-2-yl)benzyloxy)ethyl]-3-(2-phenylethoxy)propanamine hydrochloride To a solution of 1-iodo-3-(2-phenylethoxy)propane (0.566 g; 1.95 mmol) in dry THF (9 ml) is added 2-[4-(benzoxazol-2-yl)benzyloxy]ethylamine hydrochloride (0.59 g; 1.9 mmol). NaH (78 mg; 1.9 mmol) is then added at room temperature. The reaction mixture is heated at reflux for 30 minutes, then cooled, concentrated in vacuo, and the residue column chromatographed with 10% MeOH/CH$_2$Cl$_2$. The product is dissolved in EtOH acidified with HCl/EtOH concentrated to a solid and recrystallized from CH$_2$Cl$_2$/petroleum ether to obtain N-[2-(4-(benzoxazol-2-yl)benzyloxy)ethyl]-3-(2-phenylethoxy)propanamine hydrochloride. (m.p. 134°–135° C.).

EXAMPLE 37

N-[2-(4-(benzoxazol-2-yl)benzyloxy)ethyl]-2-(2-phenylethoxy)ethanamine hydrochloride Step A 2-phenylethoxyacetaldehyde To 2-(2-phenylethoxy)-1-ethanol (0.25 g; 1.5 mmol) [*J. Med. Chem.*, 1570 (1983)] dissolved in DMSO/CH$_2$Cl$_2$ (4 ml/2 ml) is added Et$_3$N (1 ml; 7 mmol) followed by sulfur trioxide pyridine complex (1.2 g; 7.5 mmol). After 10 minutes, the reaction mixture is then diluted with Et$_2$O and washed with brine, 1N HCl, NaHCO$_3$ and brine, dried (MgSO$_4$) and concentrated in vacuo to dryness. The residue is purified by column chromatography using CH$_2$Cl$_2$ to obtain 2-phenylethoxyacetaldehyde which is used directly in Step B.

Step B N-[2-(4-(benzoxazol-2-yl)benzyloxy)ethyl]-2-(2-phenylethoxy)ethanamine hydrochloride To a mixture of 2-[4-(benzoxazol-2-yl)benzyloxy)]ethylamine hydrochloride (0.11 g; 0.38 mmol) dissolved in MeOH (2 ml) and Et$_3$N (0.053 ml; 0.38 mmol) is added dried and powdered 3 Å molecular sieves along with 2-phenylethoxyacetaldehyde (0.11 g; 0.68 mmol). After 1 hour, a 1M THF solution of sodium cyanoborohydride (0.75 ml; 0.75 mmol) is added dropwise. After 2 hours, the reaction mixture is quenched with acetone and 2N HCl and then concentrated in vacuo to dryness. The residue is dissolved in 3 ml 15% NaOH, extracted with Et$_2$O 4×, dried (MgSO$_4$) and concentrated in vacuo to dryness. The residue is purified by column chromatography using 10% MeOH/CH$_2$Cl$_2$. The product is dissolved in EtOH acidified with HCl/EtOH and concentrated to yield N-[2-(4-(benzoxazol-2-yl)benzyloxy)ethyl]-2-(2-phenylethoxy)ethanamine hydrochloride as a white solid. (m.p. 174°–175° C.).

EXAMPLE 38

N-[2-(4-(benzoxazol-2-yl)benzyloxy)ethyl]-2-(trans,trans-3,7-dimethyl-2,6-octadienyloxy)ethanamine hydrochloride Step A N-trityl-N-[2-(4-(benzoxazol-2-yl)benzyloxy)ethyl]-2-(trans,trans-3,7-dimethyl-2,6-octadienyloxy)ethanamine A suspension of KH (95 mg; 0.84 mmol), THF (2.5 ml) at 0° C. and N-trityl-N-[2-(4-(benzoxazol-2-yl)benzyloxy)ethyl]-2-hydroxyethanamine (0.31 g; 0.559 mmol) is stirred 15 minutes at room temperature. To this is added geranyl bromide (0.11 ml; 0.56 mmol) dropwise. After 2 hours, the reaction mixture is quenched with EtOH, diluted with CH$_2$Cl$_2$ washed with H$_2$O and brine, dried (Na$_2$SO$_4$) and concentrated to dryness. The residue is purified by column chromatography using 5% Et$_3$N, 5% CH$_2$Cl$_2$, 90% hexanes to obtain N-trityl-N-[2-(4-(benzoxazol-2-yl)benzyloxy)ethyl]-2-(trans, trans-3,7-dimethyl-2,6-octadienyloxy)ethanamine as an oil which is used directly in Step B.

Step B N-[2-(4-(benzoxazol-2-yl)benzyloxy)ethyl]-2-(trans,trans-3,7-dimethyl-2,6-octadienyloxy)ethanamine hydrochloride N-trityl-N-[2-(4-(benzoxazol-2-yl)benzyloxy)ethyl]-2-(trans, trans-3,7-dimethyl-2,6-octadienyloxy)ethanamine (200 mg) is dissolved in MeOH (6 ml) and CH$_2$Cl$_2$ (2 ml). A solution of HCl/MeOH is added dropwise until the solution is acidic by pH paper. The reaction mixture is stirred 5 minutes, concentrated to dryness and purified by column chromatography using 5% to 10% MeOH/CH$_2$Cl$_2$. The residue is dissolved in MeOH, re-acidified with HCl/MeOH and concentrated to dryness to obtain N-[2-(4-(benzoxazol-2-yl)benzyloxy)ethyl]-2-(trans, trans-3,7-dimethyl-2,6-octadienyloxy)]ethanamine hydrochloride (m.p. 125°–128° C.).

EXAMPLE 39

1-[4-(benzoxazol-2-yl)benzyloxy]-3-(4-phenylbutoxy)-2-propanamine hydrochloride Step A t-butyldimethylsilyloxy serine methyl ester Serine methyl ester hydrochloride [HOCH$_2$CH(NH$_2$)CO$_2$CH$_3$·HCl] (18.7 g; 0.120 mol) and imidazole (30 g; 0.44 mol) are dissolved in DMF (100 ml) and cooled to 0° C. t-Butyldimethylsilyl chloride (19.5 g; 0.13 mol) is added and the reaction allowed to stir 15 hours at 25° C. The reaction is then diluted with ether (2 L), washed with water (4×500 ml), dried (MgSO$_4$) and concentrated to yield t-butyldimethylsilyloxyserine methyl ester as an oil which is used directly in Step B.

Step B N-trityl-t-butyldimethylsilyloxy serine methyl ester

To t-butyldimethylsilyloxyserine methyl ester (27.5 g; 0.118 mol) dissolved in CH$_2$Cl$_2$ (125 ml) and diisopropylethylamine (25 ml; 0.14 mol) and cooled to 0° C. is added tritylchloride (33 g; 0.118 mol) portionwise over 2 minutes. The reaction is stirred for 4 hours at 25° C., diluted with CH$_2$Cl$_2$ and washed with H$_2$O 3×. The organic phase is dried (MgSO$_4$) and concentrated to dryness to give N-trityl-t-butyldimethylsilyloxy serine methyl ester as a tan solid which is used directly next Step C.

Step C N-trityl-1,3-dihydroxy-2-propanamine

To dry ethyl ether (300 ml) is added with stirring lithium aluminum hydride (4.5 g; 0.12 mol) and cooled to 0° C. under nitrogen. The N-trityl-t-butyldimethylsilyloxy serine methyl ester (57 g; 0.12 mol) is added portionwise over 5 minutes as a solid. The reaction mixture is allowed to warm and stir for 30 minutes at 25° C. The mixture is quenched by slow addition of H₂O (4.5 ml) at 0° C. followed by 15% NaOH (4.5 ml) and H₂O (13.5 ml) at 25° C. After stirring for 3 hours, the mixture is filtered and the solid washed with THF. The combined filtrates are concentrated to which is added ether and petroleum ether to precipitate N-trityl-1,3-dihydroxy-2-propanamine which is used directly in Step D.

Step D N-trityl-1-[4-(benzoxazol-2-yl)benzyloxy]-3-hydroxy-2-propanamine

N-trityl-1,3-dihydroxy-2-propanamine (3.7 g; 11 mmol) is dissolved in THF (22 ml) and cooled to 0° C. NaH (0.44 g; 11 mmol; 60% in oil) is added and the reaction is warmed to room temperature and allowed to stir for 2 hours. 4-(benzoxazol-2-yl)benzylbromide (1.6 g; 5.5 mmol) is added and the reaction allowed to stir for 15 hours.. The reaction is diluted with CH₂Cl₂ and washed with H₂O 2×, dried (Na₂SO₄), concentrated and purified by column chromatography with basic alumina and eluted with 2% MeOH/98% CH₂Cl₂ to obtain N-trityl-1-[4-(benzoxazol-2-yl)benzyloxy]-3-hydroxy-2-propanamine as a white solid which is used directly in Step E.

Step E N-trityl-1-[4-(benzoxazol-2-yl)benzyloxy]-3-(4-phenylbutoxy)-2-propanamine N-trityl-1-[4-(benzoxazol-2-yl)benzyloxy]-3-hydroxy-2-propanamine (0.4 g; 0.74 mmol) is added to a suspension of potassium hydride (0.12 g; 1.1 mmol; 35% suspension in oil) in dry THF (4 ml) at 0° C. The reaction is stirred for 15 minutes at 20° C. 4-Phenyl-1-butyl iodide (0.21 g; 0.81 mmol) is added and the reaction mixture stirred for 15 hours. The reaction is quenched with MeOH, diluted with CH₂Cl₂ and washed with water 2×. The organic phase is dried (Na₂SO₄), concentrated and purified by column chromatography with 80% CH₂Cl₂/20% petroleum ether to yield N-trityl-1-[4-(benzoxazol-2-yl)benzyloxy]-3 -(4-phenylbutoxy)-2-propanamine as an oil which is used directly in Step F.

Step F 1-[4-(benzoxazol-2-yl)benzyloxy]-3-(4-phenylbutoxy)-2 -propanamine hydrochloride N-trityl-1-[4-(benzoxazol-2-yl)benzyloxy]-3-(4-phenylbutoxy)-2 -propanamine (0.3 g; 0.45 mmol) is dissolved in CH₂Cl₂ (3 ml) and MeOH (3 ml) and acidified to pH3 with acidic methanol. The reaction is stirred 1.5 hours, concentrated and purified by column chromatography with 8% MeOH/CH₂Cl₂. The product is isolated, dissolved in MeOH and acidified with acidic methanol. The solution is concentrated to yield 1-[4-(benzoxazol-2-yl)benzyloxy]-3-(4-phenylbutoxy)-2-propanamine hydrochloride (m.p. 125°–126° C.).

EXAMPLE 40

When the procedures of Example 39 are followed and 4-phenyl-1-butyl iodide of Step E is replaced by 3-phenyl-1-propyl iodide, 5-phenyl-1-pentyl iodide and 6-phenyl-1-hexyl iodide then the products prepared are 1-[4-(benzoxazol-2-yl)benzyloxy]-3-(3-phenylpropoxy)-2-propanamine hydrochloride (m.p. 131°–133° C.), 1-[4-(benzoxazol-2-yl)benzyloxy]-3-(5-phenylpentoxy)-2-propanamine hydrochloride. (m.p. 102°–104° C.) and 1-[4-(benzoxazol-2-yl)benzyloxy]-3-(6-phenylhexoxy)-2-propanamine hydrochloride (m.p. 170°–173° C.).

EXAMPLE 41

When the procedures of Example 39 are followed and 4-phenyl-1-butyl iodide is replaced by 3-bromo-1-phenyl-1-propene, then the product prepared is 1-[4-(benzoxazol-2-yl)benzyloxy]-3-(3-phenylpropen-2-(E )-yloxy)-2-propanamine hydrochloride (m.p. 113°–114° C.).

EXAMPLE 42

2-[4-(benzoxazol-2-yl)phenyl]-1-ethanamine hydrochloride

Step A 4-(benzoxazol-2-yl)benzyl azide

To a solution of 4-(benzoxazol-2-yl)benzyl bromide (0.49 g; 1.7 mmol) in THF (3 ml) is added sodium azide (0.22 g; 3.4 mmol) and dimethylsulfoxide (1 ml). The reaction is stirred for 24 hours and diluted with CH₂Cl₂, washed with H₂O 3× and brine, dried (MgSO₄) and concentrated in vacuo. The product is purified by column chromatography using 50% CH₂Cl₂/petroleum ether to yield 4-(benzoxazol-2-yl)benzylazide as a white solid which is used directly in Step B.

Step B 4(benzoxazol-2-yl)benzylamine hydrochloride 4-(Benzoxazol-2-yl)benzyl azide (0.22 g; 0.88 mmol) is dissolved in THF (4 ml) and MeOH (4 ml) and the reaction purged with argon. Palladium on carbon (5% by weight) (0.5 g) is added and the reaction is again purged with argon. Hydrogen is introduced and the reaction is purged with H₂. After 1 hour, the reaction is purged with argon and filtered through celite and washed with THF. The filtrate is acidified with acidic methanol and concentrated to dryness. The solid is recrystallized from MeOH to yield 4-(benzoxazol-2-yl)benzylamine hydrochloride (m.p. 250° C. dec.).

Step C 4-(benzoxazol-2-yl)benzyl cyanide

To a solution of 4-(benzoxazol-2-yl)benzyl bromide (0.5 g; 1.7 mmol) in THF (3 ml) and DMSO (3 ml) is added potassium cyanide (0.22 g; 3.4 mmol) and the reaction is stirred for 72 hours. The reaction is diluted with CH₂Cl₂, washed with H₂O 3×, dried (MgSO₄) and concentrated to dryness. The residue is purified by column chromatography using methylene chloride to yield 4-(benzoxazol- 2-yl)-benzyl cyanide which is used directly in Step D.

Step D 2-[4-(benzoxazol-2-yl)phenyl]-1-ethanamine hydrochloride

Aluminum chloride (0.2 g; 1.5 mmol) is added to a suspension of lithium aluminum hydride (60 mg; 1.5 mmol) in dry ether (6 ml) at 0° C. The reaction is stirred for 10 minutes at 20° C. and cooled to 0° C. A solution of 4-(benzoxazol-2-yl)benzyl cyanide (0.24 g; 1.02 mmol) in dry THF (4 ml) is added dropwise and the reaction is stirred at 20° C. for 2 hours. The reaction is quenched with H₂O, diluted with ether and washed vigorously with 2N HCl. The ether is decanted and the aqueous layer is washed with ether. The aqueous phase is neutralized with 15% NaOH and extracted with CH₂Cl₂. The extracts are concentrated and purified with column chromatography using CH₂Cl₂ to 20% MeOH/CH₂Cl₂. The product is acidified with acidic methanol and concentrated to yield 2-[4-(benzoxazol- 2-yl)phenyl]-1-ethanamine hydrochloride (m.p. 250° C. dec.).

EXAMPLE 43

3-[4-(benzoxazol-2-yl)phenyl]-1-propanamine hydrochloride

Step A 3-(4-bromophenyl)propargyl alcohol

To a degassed solution of 1-bromo-4-iodobenzene (5.07 g; 17.9 mmol), copper (I) iodide (68 mg; 0.36 mmol), bis(triphenylphosphine)palladium (II) chloride (0.12 g; 0.18 mmol) and diethylamine (3.7 ml; 36 mmol) in THF (90 ml) is added propargyl alcohol (1 ml; 18 mmol). The reaction is stirred 36 hours and concentrated in vacuo. The residue is purified by column chromatography with gradient elution using CH₂Cl₂ and 2% MeOH/98% CH₂Cl₂ to yield 3-(4- bromophenyl)propargyl alcohol which is used directly in Step B.

Step B 3-[4-(benzoxazol-2-yl)phenyl]propargyl alcohol

To a solution of 3-(4-bromophenyl)propargyl alcohol (11.2 g; 53.1 mmol) in dry THF (260 ml) at −78° C. is added a solution of butyllithium in hexanes (70 ml; 110 mmol) dropwise over 45 minutes. The reaction is allowed to stir an additional 30 minutes and a solution of 2-chlorobenzoxazole (6.7 ml; 58 mmol) in THF (30 ml) is added dropwise over 15 minutes. The bath is removed and the mixture is allowed to warm to 0° C. and stirred 20 minutes. MeOH (20 ml) is added slowly followed by $H_2O$ (250 ml). The mixture is extracted with ether and the organic phase is concentrated and washed with hexane and $CH_2Cl_2$ to give 3-[4-(benzoxazol-2-yl)phenyl]propargyl alcohol which is used directly in Step C.

Step C 3-[4-(benzoxazol-2-yl)phenylpropargyl p-toluenesulfonate

A solution of 3-[4-(benzoxazol-2-yl)phenyl]propargyl alcohol (1.1 g; 5.2 mmol), triethylamine (1.1 ml; 7.8 mmol), 4-(dimethylamino)pyridine (25 mg; 0.2 mmol) and p-toluenesulfonylchloride (0.99 g; 5.2 mmol) in methylene chloride (20 ml) is stirred 1 hour. The reaction is diluted with $CH_2Cl_2$, washed with 1N HCl and $NaHCO_3$, dried ($MgSO_4$), concentrated in vacuo and purified by column chromatography using $CH_2Cl_2$ to give 3-[4-(benzoxazol-2-yl)phenyl]propargyl p-toluenesulfonate which is used directly in Step D.

Step D 3-[4-(benzoxazol-2-yl)phenyl]propargyl azide

When 4-(benzoxazol-2-yl)benzyl bromide of Example 42A is replaced with 3-[4-(benzoxazol-2-yl)phenyl]propargyl p-toluenesulfonate, then the product prepared is 3-[4-(benzoxazol-2-yl)phenyl]propargyl azide which is used directly in Step E.

Step E 3-[4-(benzoxazol-2-yl)phenyl]-1-propanamine hydrochloride

When 4-(benzoxazol-2-yl)benzyl azide of Example 42B is replaced with 3-[4-(benzoxazol-2-yl)phenyl]propargyl azide, then the product prepared is 3-[4-(benzoxazol-2-yl)phenyl]-1-propanamine hydrochloride (m.p. 250° C.).

EXAMPLE 44

Step A

When 1-bromo-4-iodobenzene in Example 43, Step A is replaced by 1-bromo-3-methyl-4-iodobenzene or 1-bromo-3,6-dimethyl-4-iodobenzene, then the corresponding products are obtained.

Step B

When 2-chlorobenzoxazole in Example 43, Step B is replaced by the following compounds, then the corresponding product is prepared.

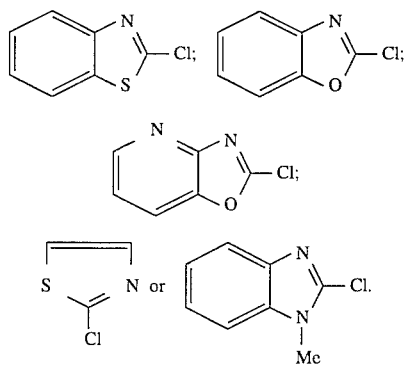

Step C

When the procedure of Example 43, Step B is followed and 2-chlorobenzoxazole is replaced by the compounds of Example 44, Step B above, and 3-(4-bromophenyl)propargyl alcohol is replaced by the compounds of Example 44, Step A above, then the corresponding compounds are prepared.

Step D

When the compounds prepared in Example 44, Steps B and C are substituted for 3-[4-benzoxazol-2-yl)phenyl]propargyl alcohol, then the corresponding product is prepared.

Step E

When the compounds prepared in Example 44, Step D above, are substituted for 4-(benzoxazol-2-yl)benzyl bromide, then the corresponding product is prepared.

Step F

When the compounds prepared in Example 44, Step E above, are substituted for 4-(benzoxazol-2-yl)benzyl azide, then the corresponding product is prepared.

EXAMPLE 45

3-[4-(benzoxazol-2-yl)phenyl]butylamine

Step A 3-[4-(benzoxazol-2-yl)phenyl]-1-propyl alcohol

3-[4-(Benzoxazol-2-yl)phenyl]propargyl alcohol (0.4 g; 2.1 mmol) is dissolved in THF (5 ml) and MeOH (10 ml) in an inert atmosphere purged by argon and then 70 mg of 5% Pd/C is added. The reaction is flushed with argon and then $H_2$, stirred for 30 minutes, purged with argon and filtered through celite and washed with MeOH and THF. The filtrate is concentrated in vacuo to yield 3-[4-(benzoxazol-2-yl)phenyl]-1-propyl alcohol which is used directly in Step B.

Step B 3-[4-(benzoxazol-2-yl)phenyl]propyl p-toluenesulfonate

When 3-[4-(benzoxazol-2-yl)phenyl]propargyl alcohol of Example 43, Step C is replaced with 3-[4-(benzoxazol-2-yl)phenyl]-1-propyl alcohol, then the product prepared is 3-[4-(benzoxazol-2-yl)phenyl]propyl p-toluenesulfonate which is used directly in Step C.

Step C 3-[4-(benzoxazol-2-yl)phenyl]propyl cyanide

When 4-(benzoxazol-2-yl)benzyl bromide of Example 36 is replaced with 3-[4-(benzoxazol-2-yl)phenyl]propyl p-toluenesulfonate, then the product prepared is 4-[4-(benzoxazol-2-yl)phenyl]butyronitrile which is used directly in Step D.

Step D 3-[4-(benzoxazol-2-yl)phenyl]butylamine

When 4-(benzoxazol-2-yl)benzyl cyanide of Example 42, Step D is replaced by 4-[4-(benzoxazol-2-yl)phenyl]butyronitrile, then the product prepared is 4-[4-(benzoxazol-2-yl)phenyl]butylamine (m.p. 220° C. dec.).

EXAMPLE 46

2-[4-(benzoxazol-2-yl)phenoxy[ethanamine hydrochloride

Step A 4-bromo-t-butyldimethylsilyloxybenzene

To a solution of 4-bromophenol (5.1 g; 29 mmol) and imidazole (2 g; 29 mmol) in $CH_2Cl_2$ (50 ml) at 0° C. is added t-butyldimethylsilyl chloride (4.4 g; 29 mmol) and the reaction is stirred for 15 hours. This is then diluted with $CH_2Cl_2$, washed with $H_2O$, ammonium chloride solution, $NaHCO_3$, dried ($MgSO_4$) and concentrated in vacuo to yield 4-bromo-t-butyldimethylsilyloxybenzene as an oil which is used directly in Step B without further purification.

Step B 4-(benzoxazol-2-yl)phenol

To a solution of 4-bromo-t-butyldimethylsilyloxybenzene (8.3 g; 29 mmol) in THF (60 ml) at −78° C. is added a solution of butyllithium in hexane (14 ml; 35 mmol) over 10 minutes. This is allowed to stir 1 hour and 2-chlorobenzoxazole (4 ml; 35 mmol) is added dropwise over 5 minutes.

After stirring 15 minutes, the reaction is allowed to warm to 0° C. and is quenched with MeOH. This is then poured into 1N HCl and after stirring 1 hour is extracted with ethyl acetate. The organic extracts are dried (MgSO$_4$) and then concentrated to yield 4-(benzoxazol- 2-yl)phenol which is used directly in Step C.

Step C N-[2-[4-(benzoxazol-2-yl)phenoxy]ethyl]phthalimide

To a mixture of 4-(benzoxazol-2-yl)phenol (0.3 g; 1.4 mmol), N-(2-hydroxyethyl)phthalimide (0.27 g; 1.4 mmol), triphenylphosphine (0.56 g; 2.1 mmol) and THF (5 ml) is added diisopropyl azodicarboxylate (0.42 ml; 2.1 mmol). The reaction is stirred 24 hours, diluted with ethyl acetate, washed with H$_2$O, 2N HCl, NaHCO$_3$ and brine, dried (MgSO$_4$) and concentrated in vacuo to dryness. The residue is purified by gradient elution column chromatography using CH$_2$Cl$_2$ and 1% MeOH/99% CH$_2$Cl$_2$ to yield N-[2-[4-(benzoxazol-2-yl)phenoxy]ethyl]phthalimide which is used directly in Step D.

Step D 2-[4-(benzoxazol-2-yl)phenoxy]ethanamine hydrochloride

To N-[2-[4-(benzoxazol-2-yl)phenoxy]ethyl]phthalimide (89 mg; 0.25 mmol), THF (3 ml) and MeOH (1 ml) is added hydrazide hydrate (0.1 ml). The reaction is stirred 15 hours and concentrated to dryness in vacuo. The solid is extracted with 10% MeOH/90% CH$_2$Cl$_2$ and filtered. The filtrate is acidified with acidic methanol, concentrated in vacuo and the resulting solid recrystallized from MeOH to give 2-[4-(benzoxazol-2-yl)phenoxy]ethanamine hydrochloride (m.p. 280° C. dec.).

EXAMPLE 47

3-[4-(benzoxazol-2-yl)phenoxy]propanamine hydrochloride

Step A N-[3-[4-(benzoxazol-2-yl)phenoxy]propyl]phthalimide

When N-(2-hydroxyethyl)phthalimide of Example 46, Step C is replaced with N-(3-hydroxypropyl)phthalimide, then the product obtained is N-[3-[4-(benzoxazol- 2-yl)phenoxy]propyl]phthalimide.

Step B 3-[4-(benzoxazol-2-yl)phenoxy]propanamine hydrochloride

When N-[2-[4-(benzoxazol-2-yl)phenoxy]ethyl]phthalimide of Example 46, Step D is replaced by N-[3-[4-(benzoxazol-2-yl)phenoxy]propyl phthalimide, then the product prepared is 3-[4-(benzoxazol-2-yl)phenoxy]propanamine hydrochloride (m.p. 260° C. dec.).

EXAMPLE 48

1-[4-(benzoxazol-2-yl)benzyloxy]-3-(4-phenylbutoxy)-2propanamine hydrochloride

Step A ethyl 2-[4-(benzoxazol-2-yl)benzyl]-N-(diphenylmethylene)glycine

A mixture of N-(diphenylmethylene)glycine ethyl ester (6.85 g; 25.6 mmol), 4-(benzoxazol-2-yl)benzyl bromide (7.37 g; 25.6 mmol), tetrabutylammonium bromide (0.83 g; 2.6 mmol); potassium carbonate (10.6 g; 77 mmol) and dry acetonitrile (50 ml) is heated at reflux 4 hours. The reaction is cooled and diluted with CH$_2$Cl$_2$, washed with water, dried (Na$_2$SO$_4$) and concentrated in vacuo to yield ethyl 2-[4-(benzoxazol-2yl)benzyl]-N-(diphenylmethylene)glycine as an oil which is used directly without further purification in Step B.

Step B ethyl 2-[4-(benzoxazol-2-yl)benzyl]glycine hydrochloride

A solution of ethyl 2-[4-(benzoxazol-2-yl)benzyl]-N-(diphenylmethylene)glycine (3.2 g; 6.7 mmol) in EtOH (34 ml) is acidified with acidic ethanol and allowed to stir 15 hours. The reaction is treated with ether and the resulting precipitate is filtered and washed with ether to provide ethyl 2-[4-(benzoxazol-2yl)benzyl]glycine hydrochloride which is used directly in Step C.

Step C ethyl 2-[4-(benzoxazol)-2-yl)benzyl]-N-trityl-glycine

Ethyl 2-[4-(benzoxazol)-2-yl)benzyl]glycine hydrochloride (6.31 g; 18.2 mmol) is dissolved in dry methylene chloride (60 ml) and triethylamine (5 ml; 36 mmol) and cooled to 0° C. Tritylchloride (5.6 g; 20 mmol) is added and the reaction is stirred at 25° C. for 15 hours, diluted with CH$_2$Cl$_2$, washed with water and brine, dried (MgSO$_4$), concentrated and purified by column chromatography using CH$_2$Cl$_2$ to provide ethyl 2-[4-(benzoxazol-2-yl)benzyl]-N-trityl-glycine which is used directly in Step D.

Step D N-trityl-1-[4-(benzoxazol-2-yl)phenyl]-3-hydroxy-2-propanamine

To a mixture of ethyl 2-[4-(benzoxazol-2-yl)benzyl]-N-trityl-glycine (8.8 g; 16 mmol), dry ether (80 ml) and dry THF (40 ml) is added lithium aluminum hydride (0.8 g; 21 mmol) at 0° C. The reaction is then cooled to 0° C. and 0.8 ml H$_2$O is added slowly, followed by 0.8 ml of 15% NaOH and then 2.4 ml H$_2$O . This is brought to 25° C. and stirred 15 hours. The reaction is filtered through a bed of celite and extracted with ether and THF. The filtrate is concentrated to an oil which solidifies upon treatment with MeOH and Et$_2$O. The solid is recrystallized from MeOH to yield N-trityl-1-[4-(benzoxazol-2-yl)phenyl]-3-hydroxy-2-propanamine.

Step E N-trityl-1-[4-benzoxazol-2-yl)phenyl]-3-(4-phenylbutoxy)-2-propanamine

When N-trityl-1-[4-(benzoxazol-2-yl)benzyloxy]-3-hydroxy-2-propanamine of Example 39, Step E is replaced with N-trityl-1-[4-(benzoxazol-2-yl)phenyl]-3-hydroxy-2-propanamine, then the product prepared is N-trityl-1-[4-benzoxazol-2-yl)phenyl]-3-(4-phenylbutoxy)-2-propanamine.

Step F 1-[4-(benzoxazol-2-yl)benzyloxy]-3-(4-phenylbutoxy)-2-propanamine hydrochloride When N-trityl-1-[4-(benzoxazol-2-yl)benzyloxy]-3-(4-phenylbutoxy)-2-propanamine of Example 39, Step F is replaced with N-trityl-1-[4-(benzoxazol-2-yl)phenyl]-3-(4-phenylbutoxy)-2-propanamine, then the product prepared is 1-[4-(benzoxazol- 2-yl)benzyloxy]-3-(4-phenylbutoxy)-2-propanamine hydrochloride.

EXAMPLE 49

When the procedure of Example 34, Step F is followed and 6-phenyl-1-hexyliodide is replaced by 6-phenyl-2-heptyliodide, 5-phenyl-1-pentytliodide, 5-phenyl-2-hexyliodide'

7-phenyl-1-heptyliodide or 7-phenyl-3-heptyliodide and N-[2-(4-(benzoxazol-2-yl)benzyloxy)ethyl]amine hydrochloride is replaced by the compounds of Example 44, Step F, then the corresponding product is prepared.

Various tests have been carried out to show the ability of the compounds of the present invention to exhibit pharmacological responses that can be correlated with activity in humans. These tests involve such factors as the effect of the compounds of Formula I to inhibit squalene synthesis. It has been found that compounds within the scope of this invention when tested using the following procedures show a marked activity for the inhibition of squalene synthase and hence are believed to be useful in the treatment of cholesterol-related disorders.

Squalene Synthase Inhibition Assay

The squalene synthase assay used is a modification of the procedures described by Popjak (1969) and Poulter et al. (1989):

Popjak, G. Enzymes of sterol biosynthesis in liver and intermediates of sterol biosynthesis. Meth. Enzymol. 15: 393–454, 1969.

Poulter, C. D., Capson, T. L, Thompson, M. D. and Bard R. S. Squalene synthase. Inhibition by ammonium analogues of carbocationic intermediates in the conversion of presqualene diphosphate to squalene. J. Am. Chem. Soc. 111: 3734–3739, 1989.

I. Animal Source and Tissue Preparation:

Four male Sprague-Dawley rats weighing 100–120 gms are fed a low cholesterol rodent diet (#5012) obtained from Purina Mills, inc. in Richmond, Ind.; and housed under reverse-light. Water is given ad lib. Rats are lightly anesthetized with ether and then decapitated. Livers are removed and enzymes are separated by the method described below.

II. Materials:

Chemicals:

All Chemicals are "A.C.S." in purity or better unless noted;

AquaSol®-2 scintillation fluid (NEF-952) (Du Pont/NEN Research Products, Boston, Mass.);

Anhydrous $MgCl_2$ (M-8266), β-NADPH tetrasodium salt, reduced form (N-1630), Bovine serum albumin (A-6003), Cholesterol (C-8503);

Squalene (S-3626), (Sigma Chemical Co., St. Louis, Mo.);

Bio-Rad protein assay dye concentrate (Bio-Rad Laboratories, Richmond, Calif.);

Denatured ethanol, DMSO, HCl (1N), KOH, methanol, NaOH (0.1N, 1N), petroleum ether (M-280 grade), potassium phosphate dibasic, 2-propanol (Fisher Scientific, Pittsburgh, Pa.);

Zero grade nitrogen gas mixture (certified analysis) (Woodland Oxygen & Supply Co., Philadelphia, Pa.).

Radiochemicals:

[1-$^3$H(N)]-FPP, triammonium salt (NET-1042), (Du Pont/NEN, Boston, Mass.);

[4,8,12,13,17,21-$^3$H]-Squalene (NET-645) (Du Pont/NEN);

Non-radiolabeled FPP is prepared in-house. The solid FPP is aliquoted and stored at −80° C. FPP is dissolved in 70% ethanol/30% 0.25M $NH_4HCO_3$ at the concentration of 10 mM and the solution is aliquoted (200 μl each) and stored at −80° C.

III. Preparation of Assay Substances:

A) Test Solutions:

Test solutions are prepared fresh in 100% DMSO or $dH_2O$. Subsequent dilutions are made in the same solvent. Compounds are tested initially at 1 or 10 μM (final concentrations).

B) Assay Buffer:

Potassium Phosphate (50 mM, 8.71 g/l), pH 7.5 stock buffer is prepared and stored at 4° C. until use. Anhydrous $MgCl_2$ is added to the phosphate buffer on the day of assay for a final concentration of 10 mM (95 mg/100 ml). The buffer is flushed with $N_2$ before use.

C) Substrate:

Non-radiolabeled FPP is diluted to 50 μM (100 μl 10 mM cold FPP +19.9 ml phosphate buffer). Then, 14 μl (20×10$^6$ dpm) of $^3$H-FPP (0.5 mCi/ml, 0.011 mg/ml) is added. 200 μl of this mixture is added per assay tube for a final reaction concentration of 10 μM FPP (~200,000 dpm/assay tube).

D) β-NADPH Solution:

37.5 mg of β-NADPH is added to 9 ml assay buffer for a 5 mM concentration of β-NADPH. The mixture is vortexed and 100 μl of this solution is added to each tube for a final assay concentration of 0.5 mM β-NADPH.

E) KOH in Ethanol:

75 gm of KOH is dissolved in 500 ml of denatured ethanol for a 15% solution and stored at 0° C. until use. 1 ml of this solution is added per tube to terminate the reaction.

IV. Experimental Procedure:

A) Enzyme Preparation:

Immediately following decapitation, livers are removed one at a time from four rats. The livers are combined and weighed in a tared beaker. Assay buffer is added equal to three times the liver weight. The liver is first homogenized with a blender for thirty seconds, and then by a motor driven Teflon pestle at a speed of 2.5. During homogenization, the liver is kept on ice. When the liver is fully homogenized, the homogenate is centrifuged at 10,000 g for 30 min. at 4° C. in 50 ml capacity centrifuge tubes. The mitochondrial pellet is discarded and the supernatant is filtered through a layer of gauze moistened with a little buffer. This supernatant is recentrifuged at 105,000 g for one hour at 0° C. in an ultracentrifuge in 25 ml capacity ultracentrifuge tubes.

Following centrifugation, the supernatant is removed and discarded. The sediment pellet consists of 2 layers: a transparent inner layer of glycogen, surrounded by an opaque brown layer of microsomes. The brown outer microsomal layer is carefully removed with a spatula and placed in a beaker on ice. Assay buffer is added in an amount equal to one half the original homogenate volume, and this mixture is poured into ultracentrifuge tubes. These tubes are recentrifuged at 105,000 g for 1 hour at 4° C.

After this centrifugation is complete, the supernatant is again removed and discarded. Fresh assay buffer is added to the combined pellets to achieve a volume equal to one tenth of the original homogenate volume. The microsomal fraction is then rehomogenized on a motor driven Teflon pestle at a speed of 2.5 to partially solubilize and make a uniform suspension of the microsomes. The enzyme (~20 ml, ~40 mg protein/ml) is aliquoted (200 μl) into eppendorf plastic tubes, capped and stored at −80° C. until use.

B) Assay Procedure

To begin the assay, 20 μl of the compound of this invention or vehicle solution is added to each 16×150 screw-cap culture tube on ice. Then 580 μl of $N_2$ flushed assay buffer is pipetted into each tube. 100 μl of cofactor is next added to each tube, followed by 100 μl of a dilution of microsomal enzyme (approximately 80 ug protein). The tubes are preincubated for 10 minutes at 37° C., and 200 μl of the $^3$H-FPP (200,000 dpm, 10 μM final conc.) is added to each tube at two second intervals. The tubes are then incubated for exactly 10 minutes, shaking at 150 oscillations per minute. After the 10 minute incubation, the reaction is stopped by the addition of 1 ml of 15% KOH in ethanol, and the tubes are incubated for 30 minutes in a 65° C. water bath for saponification of lipids and solubilization of proteins. The tubes are cooled on ice for five minutes. The samples are next extracted with 5 ml of petroleum ether by shaking for 10 minutes at low speed on a metabolic shaker. Each lower aqueous layer is frozen in a dry ice/alcohol bath (2-propanol/methanol, 1:1), and each organic layer is poured into another set of 16×150 screw-top culture tubes containing 2 ml of deionized water. Each ether layer is washed by vortexing each tube for 5 seconds. The aqueous layers are again frozen in the dry ice/alcohol bath, and the ether is poured into scintillation vials. 10 ml of AquaSol® is next added to each vial, and the vials are counted for 5 minutes in a scintillation counter. Percent inhibitions are calculated from the counts obtained.

V. Statistical Considerations

The samples are counted as dpm using a Beckman Scintillation counter (Model LS-9000). Percent inhibition is calculated using a Lotus 1-2-3 program. The $IC_{50}$ values are calculated using a linear regression program of Tallarida and Murray (1987). Tallarida, R. J. and Murray, R. B. Manual of pharmacologic calculations with computer programs. Springer-Verlag, 1987.

The following in vivo assays are used to determine the effectiveness of compounds of this invention to inhibit squalene synthase.

In Vivo Rat Method:

Forty male Sprague-Dawley rats weighing 80–90 gms are fed a low cholesterol rodent meal diet (#5012) obtained from Purina Mills, Inc. in Richmond, Ind.; and housed under reversed-light. Water is given ad lib. After a week of housing, the rats are fed cholestyramine (2% in diet) for the next 2 days. One day after the cholestyrmmine treatment, a compound is given three times to 4 rats (30 mg/kg, in 10 ml 0.5% methylcellulose/Kg, p.o.) at 8 a.m., 5 p.m. and 8 a.m. the following day. Four hours after the last dose, the rat is decapitated and blood and the liver are collected. Serum is separated and analyzed for cholesterol by an assay kit supplied by Sigma Chemical Co., St. Louis, Mo. Sterols in the serum and the liver are also analyzed by HPLC analysis. The liver cholesterol level is determined by quantitating against cholesterol as a standard by HPLC. Results are determined as the change in the liver and serum cholesterol compared to respective vehicle treated control values.

Mouse in vivo assay for cholesterol-lowering effect:

Balb-c mice weighing 20–25 gms are used for this study. Mice are fed a meal diet (RP#5012) containing 2% cholestyramine. Test compound is dissolved/suspended in 0.5% methyl cellulose and given to mice at 50 mg/kg, b.i.d. (n=8). Blood is collected from the tail on days 0 and 7 and from inf. vena cava on day 14. Body weights and the food consumption are monitored weekly. Serum cholesterol is determined by an enzyme assay kit (Sigma Chemical Co.). Serum and the liver are analyzed by HPLC for vadous sterols. Results are determined as % change from the vehicle treated controls.

HPLC Procedure

Sample preparation:

In 16×125 mm screw cap glass tubes, is added 0.5 ml serum or plasma or liver slices suspension (0.11 gm/ml buffer). To this is then added 1 ml of KOH/ethanol (15%). The glass tubes are incubated at 80° C. for 2 hours while shaking. After saponification, 10 ml petroleum ether is added to each tube and then capped. The tubes are shaken for 30 min. then frozen at −80° C. and the ether removed to 16×150 mm screw top glass tubes. Water (2 ml) is added and again the tubes am shaken for 10 minutes. After freezing, the ether is transferred into 16×125 mm glass culture tubes. The ether is evaporated under $N_2$. HPLC grade ethanol (0.5 ml) is added to the tubes, capped and shaken for 30 min. to dissolve all lipids. The ethanol is filtered using a syringe filter (pore size: 0.45 uM, Spartan-13, Schleicher & Schuell) and 50 ul of this solution is injected into HPLC.

HPLC specifications:

Column: Partisil 10 ODS-3, C-18 reversed phase, 25 cm length at 25° C. [Whatman Cat#4228-001]

Pump: Waters 6000A, Isocratic system

Solvent: Acetonitrile:water:: 95:5; 2 ml/min

Run Time: 33 min 50 ul injection by Autosampler WISP 710B, Waters/Millipore

Wavelength: 210 nm, Applied Biosystems 757 Absorbance detector

Integrator: Hewlett Packard 3396 Series II.

Typical Retention Times:

Squalene dioxide—7.5 min

Squalene oxide—14 min 7-dehydro Chol.—16 min

Cholesterol—23 min

Squalene—30 min

Compounds within the scope of Formula I have been tested by the foregoing assay procedures and exhibit marked squalene synthase inhibition activity and are useful as hypocholesterolemic or hypolipidemic agents by virtue of their ability to inhibit the biosynthesis of cholesterol. Having such ability, the compounds are incorporated into pharmaceutically acceptable carriers and administered to a patient in need of such cholesterol biosynthesis inhibition. These pharmaceutical formulations contain at least one compound according to this invention.

Treatment with a combination of an HMG-CoA reductase inhibitor and a squalene synthase inhibitor would have a synergistic effect on inhibiting cholesterol biosynthesis. Inhibiting the squalene synthase enzyme and the HMG-CoA reductase enzyme at the same time would most closely resemble the physiological conditions of cholesterol homeostasis. A squalene synthase inhibitor could keep cellular concentrations of farnesyl diphosphate high enough for the synthesis of the small amounts of dolichol, ubiquinone, and the farnesylated proteins required by the cell. This would maintain some feedback regulation of the HMG-CoA reductase enzyme and allow smaller amounts of the HMG-CoA reductase inhibitor to be used.

Other combinations with a squalene synthase inhibitor which could have a synergistic effect for controlling undesirable cholesterol levels in the body include niacin, antihyperlipoproteinemic agents such as gemfibrozil, cholesterol absorption inhibitors, bile acid sequestrants, antioxidants and lipoxygenase inhibitors.

The compounds of the present invention can be administered to a mammalian host in a variety of forms adapted to the chosen route of administration, i.e., orally, or parenterally. Parenteral administration in this respect includes administration by the following routes: intravenous, intramuscular, subcutaneous, intraocular, intrasynovial, transepithelially including transdermal, ophthalmic, sublingual and buccal; topically including ophthalmic, dermal, ocular, rectal and nasal inhalation via insufflation and aerosol and rectal systemic.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 6% of the weight of the unit. The amount of active compound in such therapeutically useful compositions is such that a suitable dosage will be obtained. Preferred compositions or preparations according to the present invention are prepared so that an oral dosage unit form contains between about 50 and 300 mg of active compound.

The tablets, trothas, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It may be stable under the conditions of manufacture and storage and must be preserved against the contaminating action of microorganisms such as bacteria and fungi. The carrier can be a solvent of dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by vadous antibacterial and antifungal agents, for example, parabens, chlorobutanol, phenol, sorbic acid, thimersal, and the like. In many cases, it will be preferable to include isotonic agents, for example, sugars or sodium chloride. Prolonged absorption of the injectable compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of this invention may be administered to a mammal alone or in combination with pharmaceutically acceptable carriers, as noted above, the proportion of which is determined by the solubility and chemical nature of the compound, chosen route of administration and standard pharmaceutical practice.

The physician will determine the dosage of the present therapeutic agents which will be most suitable for prophylaxis or treatment and it will vary with the form of administration and the particular compound chosen, and also, it will vary with the particular patient under treatment. He will generally wish to initiate treatment with small dosages by small increments until the optimum effect under the circumstances is reached. The therapeutic dosage will generally be from about 0.1 to about 100 mg/kg/dy, and preferably from about 10 mg to about 1000 mg day, or from about 0.1 mg to about 50 mg/kg of body weight per day and preferably from about 0.1 to about 20 mg/kg of body weight per day and may be administered in several different dosage units. Higher dosages on the order of about 2× to about 4× are required for oral administration.

We claim:

1. A compound of the formula:

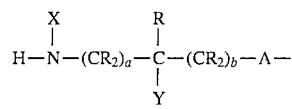

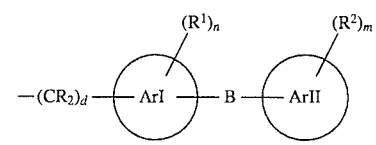

where:

X is hydrogen or $-(CH_2)_2(CR_2)_f-D-E$ and

Y is hydrogen or $-(CR_2)_h-D-G$ provided one of X or Y is hydrogen;

A is O, S, NR, SO, $SO_2$, O=C, NR—C=O, O=C—NR, RC=CR, C≡C or a bond;

B is $(CR_2)_e$, O, S, NR, SO, $SO_2$, NR—C=O, O=C—NR, RC=CR, C≡C, O=C or a bond;

D is O, S, NR, SO, $SO_2$, O=C, $CH_2$, RC=CR or a bond;

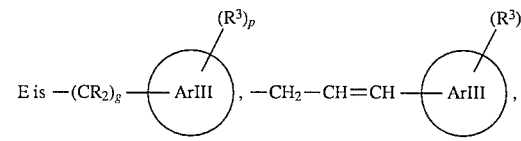

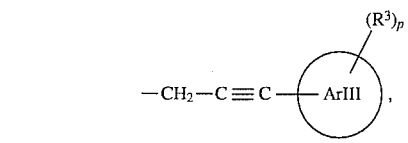

$CH_2-CH=CR-CH_2-CH_2-CH=CR-CH_3$
or
$CH_2-CR=CH-CH_2-CH_2-CR=CH-CH_3$;

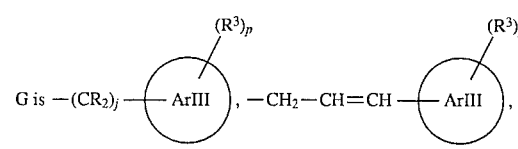

-continued

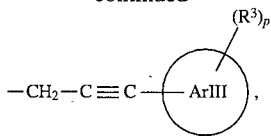

CH₂—CH=CR—CH₂—CH₂—CH=CR—CH₃
or
CH₂—CR=CH—CH₂—CH₂—CR=CH—CH₃

R is hydrogen or alkyl;

R¹, R² and R³ are independently hydrogen, alkyl, alkoxy, hydroxy, halo, haloalkyl, nitro, amino, mono- or di-alkylamino or phenyl;

Ar I is

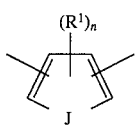

Ar II is

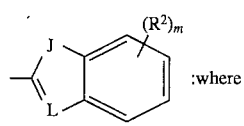 :where

J is CH=CH; and
L is N; and
Ar III is

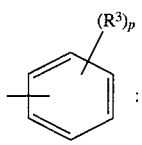 ;

a, b and d are independently 0–3;
a+b+d is 1–3;

e is 1–3;
f and g are independently 0–4;
f+g is 3 or 4 when f and g are both present;
h and j are 0–6;
h+j is 6 or 7 when h and j are both present; and
m, n and p are 0–2; and its stereoisomers, enantiomers, diastereoisomer and racemic mixtures; or pharmaceutically acceptable salt thereof.

2. A compound according to claim 1 of the formula:

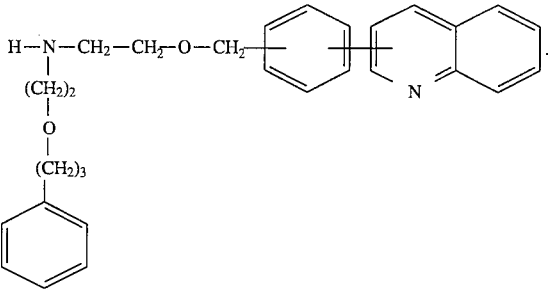

3. A method of lowering or maintaining reduced cholesterol levels in a patient requiring such treatment which comprises administering to such patient a squalene synthase inhibitor effective amount of a compound of the formula according to claim 1.

4. A method for inhibiting cholesterol biosynthesis which comprises administering to a patient in need of such inhibition a squalene synthase inhibiting effective amount of a compound according to claim 1.

5. A method according to claim 4 where the patient is in need of a hypocholesterolemic or hypolipidemic agent.

6. A method according to claim 5 for treating atherosclerosis.

7. A pharmaceutical composition comprising a squalene synthetase inhibitor effective amount of a compound according to claim 1 in admixture with a pharmaceutical carrier.

8. A pharmaceutical composition according to claim 7 which further includes an HMG CoA reductase inhibitor.

* * * * *